(12) United States Patent
Delany et al.

(10) Patent No.: US 9,657,297 B2
(45) Date of Patent: May 23, 2017

(54) PROMOTERS FOR INCREASED PROTEIN EXPRESSION IN MENINGOCOCCUS

(71) Applicant: GlaxoSmithKline Biologicals SA, Rixensart (BE)

(72) Inventors: Isabel Delany, Siena (IT); Serafina Guadagnuolo, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 14/375,222

(22) PCT Filed: Feb. 1, 2013

(86) PCT No.: PCT/EP2013/052108
§ 371 (c)(1),
(2) Date: Jul. 29, 2014

(87) PCT Pub. No.: WO2013/133917
PCT Pub. Date: Aug. 8, 2013

(65) Prior Publication Data
US 2015/0218566 A1 Aug. 6, 2015

Related U.S. Application Data

(60) Provisional application No. 61/594,159, filed on Feb. 2, 2012.

(51) Int. Cl.
| | | |
|---|---|---|
| C07H 21/02 | (2006.01) |
| C07H 21/04 | (2006.01) |
| C12N 15/74 | (2006.01) |
| C07K 14/22 | (2006.01) |
| A61K 39/095 | (2006.01) |

(52) U.S. Cl.
CPC ............ *C12N 15/74* (2013.01); *A61K 39/095* (2013.01); *C07K 14/22* (2013.01); *C12N 2800/60* (2013.01)

(58) Field of Classification Search
None
See application file for complete search history.

(56) References Cited

U.S. PATENT DOCUMENTS

| | | | |
|---|---|---|---|
| 4,551,433 | A | 11/1985 | DeBoer et al. |
| 5,698,438 | A | 12/1997 | Stojiljkovic et al. |
| 6,180,111 | B1 | 1/2001 | Stein et al. |
| 6,531,131 | B1 | 3/2003 | Gu et al. |
| 6,645,503 | B1 | 11/2003 | Arumugham et al. |
| 2002/0160016 | A1 | 10/2002 | Peak et al. |
| 2003/0224012 | A1 | 12/2003 | Ruelle et al. |
| 2004/0126389 | A1 | 7/2004 | Berthet et al. |
| 2004/0147474 | A1 | 7/2004 | Ruelle et al. |
| 2004/0265330 | A1 | 12/2004 | Ruelle et al. |
| 2004/0265878 | A1 | 12/2004 | Ruelle et al. |
| 2005/0075485 | A1 | 4/2005 | Ruelle et al. |
| 2007/0031449 | A1 | 2/2007 | Bos et al. |
| 2008/0248065 | A1 | 10/2008 | Granoff et al. |
| 2009/0035328 | A1 | 2/2009 | Granoff et al. |
| 2009/0247428 | A1 | 10/2009 | Duncum et al. |
| 2010/0184139 | A1 | 7/2010 | Defrenne et al. |

FOREIGN PATENT DOCUMENTS

| | | |
|---|---|---|
| CA | 1142083 | 1/1983 |
| EP | 0011243 | 5/1980 |
| WO | WO-96/29412 | 9/1996 |
| WO | WO-99/10497 | 3/1999 |
| WO | WO-99/57280 | 11/1999 |
| WO | WO-00/11182 | 3/2000 |
| WO | WO-00/23595 | 4/2000 |
| WO | WO-00/25811 | 5/2000 |
| WO | WO-00/26384 | 5/2000 |
| WO | WO-00/42191 | 7/2000 |
| WO | WO-00/43517 | 7/2000 |
| WO | WO-00/43518 | 7/2000 |
| WO | WO-00042192 | 7/2000 |
| WO | WO-00/44890 | 8/2000 |
| WO | WO-00/44904 | 8/2000 |
| WO | WO-00/47743 | 8/2000 |
| WO | WO-00/66741 | 11/2000 |
| WO | WO-01/09339 | 2/2001 |
| WO | WO-01/09350 | 2/2001 |
| WO | WO-01/30390 | 5/2001 |
| WO | WO-01/34642 | 5/2001 |
| WO | WO-01/38350 | 5/2001 |
| WO | WO-01/55182 | 8/2001 |
| WO | WO-01/91788 | 12/2001 |
| WO | WO-02/09643 | 2/2002 |
| WO | WO-02/09746 | 2/2002 |
| WO | WO-02/062378 | 8/2002 |
| WO | WO-02/083723 | 10/2002 |

(Continued)

OTHER PUBLICATIONS

Amann et al. (1983). "Vectors Bearing a Hybrid Trp-Lac Promoter Useful for Regulated Expression of Cloned Genes in *Escherichia coli*," Gene, 25(2-3):167-78.

Arhin et al. (1998). "Sequencing of porA from clinical isolates of Neisseria meningitidis defines a subtyping scheme and its genetic regulation," Canadian Journal of Microbiology, 44(1):56-63.

Bonvehi et al. (2010). "Three doses of an experimental detoxified L3-derived lipooligosaccharide meningococcal vaccine offer good safety but low immunogenicity in healthy young adults," Clin Vacc Immunol, 17(9):1460-1466.

(Continued)

*Primary Examiner* — Jennifer Graser

(57) ABSTRACT

New promoters are described to drive transcription in meningococcus e.g. for over-expression of protein antigens for retention in membrane vesicles. Modified porA promoters lack the wild-type poly-G sequence which can cause phase variation. Meningococcal rRNA-coding genes (e.g. for 16S rRNA) can be used to drive transcription of a protein-coding gene. These approaches can be used in combination.

15 Claims, 5 Drawing Sheets

(56) References Cited

FOREIGN PATENT DOCUMENTS

| | | |
|---|---|---|
| WO | WO-03/063766 | 8/2003 |
| WO | WO-03/105890 | 12/2003 |
| WO | WO-2004/014417 | 2/2004 |
| WO | WO-2004/014418 | 2/2004 |
| WO | WO-2004/015099 | 2/2004 |
| WO | WO-2004/019977 | 3/2004 |
| WO | WO-2004/048404 | 6/2004 |
| WO | WO-2005/004908 | 1/2005 |
| WO | WO-2006/024946 | 3/2006 |
| WO | WO-2006/046143 | 5/2006 |
| WO | WO-2006/081259 | 8/2006 |
| WO | WO-2007/000327 | 1/2007 |
| WO | WO-2007/071707 | 6/2007 |
| WO | WO-2009/038889 | 3/2009 |
| WO | WO-2009/104097 | 8/2009 |
| WO | WO-2009/114485 | 9/2009 |
| WO | WO-2009/158142 | 12/2009 |
| WO | WO-2010/025964 | 3/2010 |
| WO | WO-2010/046715 | 4/2010 |
| WO | WO-2010/070453 | 6/2010 |
| WO | WO-2010/127172 | 11/2010 |
| WO | WO-2011/036562 | 3/2011 |
| WO | WO-2011/126863 | 10/2011 |
| WO | WO-2013/033398 | 3/2013 |

OTHER PUBLICATIONS

Brusic et al. (1998). "Prediction of MHC class II-binding peptides using an evolutionary algorithm and artificial neural network," Bioinformatics, 14(2):121-30.

Bublil et al. (2007). "Stepwise prediction of conformational discontinuous B-cell epitopes using the Mapitope algorithm," Proteins, 68(1):294-304.

Cantini et al. (2006). "Solution structure of the immunodominant domain of protective antigen GNA1870 of Neisseria meningitides," J Biol. Chem. 28(11):7220-7227.

Carter. (1994). "Epitope mapping of a protein using the Geysen (PEPSCAN) procedure," Methods Mol Biol., 36:207-23.

Chen et al. (2007). "Prediction of linear B-cell epitopes using amino acid pair antigenicity scale," Amino Acids, 33(3):423-428.

Claassen et al. (1996). "Production, characterization and control of a Neisseria meningitidis hexavalent class 1 outer membrane protein containing vesicle vaccine," Vaccine, 14: 1001-1008.

Davenport et al. (1995). "An empirical method for the prediction of T-cell epitopes," Immunogenetics, 42(5):392-297.

de Boer et al. (1983). "The Tac Promoter: A Functional Hybrid Derived From the Trp and Lac Promoters," PNAS, 80:21-25.

de Kleijn et al. (2000). "Immunogenicity and safety of a hexavalent meningococcal outer-membrane-vesicle vaccine in children of 2-3 and 7-8 years of age," Vaccine, 18(15): 1456-6146.

de Lalla et al. (1999). "Cutting edge: identification of novel T cell epitopes in Lol p5a by computational prediction," J Immunol., 163:1725-29.

Deghmane et al. (2003). "Differential expression of genes that harbor a common regulatory element in Neisseria meningitidis upon contact with target cells," Infect Immun., 71:2897-901.

Donnelly et al. (2010). "Qualitative and quantitative assessment of meningococcal antigens to evaluate the potential strain coverage of protein-based vaccines," PNAS USA, 107(45):19490-19495.

Feller et al. (1991). "Identifying antigenic T-cell sites," Nature 349(6311):720-721.

Fletcher et al. (2004). "Vaccine potential of the Neisseria meningitidis 2086 lipoprotein," Infect Immun, 72(4):2088-2100.

Fredriksen et al. (1991). "Production, characterization and control of MenB-vaccine 'Folkehelsa': an outer membrane vesicle vaccine against group B meningococcal disease," NIPH Ann., 14(2):67-80.

Geysen et al. (1984). "Use of peptide synthesis to probe viral antigens for epitopes to a resolution of a single amino acid," PNAS USA, 81(13):3998-4002.

Giuliani et al. (2006). "A universal vaccine for serogroup B meningococcus," Proc Natl Acad Sci USA, 103(29):10834-10839.

Gorla et al. (2003). "Comparison of PorA VR types and porA promoter sequence from Neisseria meningitidis B isolated from non-immunised children and vaccine failures immunised with a serogroup B outer membrane protein vaccine," Vaccine, 21(21-22):2871-2876.

Gourse et al. (1986). "DNA determinants of rRNA synthesis in *E. coli*: growth rate dependent regulation, feedback inhibition, upstream activation, antitermination," Cell 44(1):197-205.

Hirvonene et al. (2001). "Contributions of UP elements and the transcription factor FIS to expression from the seven rrn P1 promoters in *Escherichia coli*," J Bacteriol., 183(21):6305-14.

Hopp. (1993). "Retrospective: 12 years of antigenic determinant predictions, and more," Peptide Research 6(4):183-190.

Hou et al. (2005). "Protective antibody responses elicited by a meningococcal outer membrane vesicle vaccine with overexpressed genome-derived neisserial antigen 1870," J Infect Dis, 192(4):580-90.

Jameson et al. (1988) "The antigenic index: a novel algorithm for predicting antigenic determinants," Comput Appl Biosci, 4(1):181-186.

Katial et al. (2002). "Immunogenicity and safety testing of a group B intranasal meningococcal native outer membrane vesicle vaccine," Infect. Immun., 70(2):702-707.

Keiser et al. (2011). "A phase 1 study of a meningococcal native outer membrane vesicle vaccine made from a group B strain with deleted lpxL1 and synX, over-expressed factor H binding protein, two PorAs and stabilized OpcA expression," Vaccine, 29(7):1413-1420.

Kimura et al. (2010). "Immunogenicity and safety of a multicomponent meningococcal serogroup B vaccine and a quadrivalent meningococcal CRM197 conjugate vaccine against serogroups A, C, W-135, and Y in adults who are at increased risk for occupational exposure to meningococcal isolates," Clin Vaccine Immunol., 18(3):483-486.

Koeberling et al. (2007). "Improved immunogenicity of a H44/76 group B outer membrane vesicle vaccine with over-expressed genome-derived Neisserial antigen 1870," *Vaccine*, 25(10):1912-1920.

Koeberling et al. (2008). "Bactericidal antibody responses elicited by a meningococcal outer membrane vesicle vaccine with overexpressed factor H-binding protein and genetically attenuated endotoxin," J Infect Dis, 198(2):262-70.

Koeberling et al. (2009). "Meningococcal Outer Membrane Vesicle Vaccines Derived from Mutant Strains Engineered to Express Factor H Binding Proteins from Antigenic Variant Groups 1 and 2," Clin and Vacc Immun, 156-162.

Koeberling et al. (2011). "Immunogenicity of a meningococcal native outer membrane vesicle vaccine with attenuated endotoxin and over-expressed factor H binding protein in infant rhesus monkeys," Vaccine, 29:4728-34.

Kwok et al. (2001). "Rapid epitope identification from complex class-II-restricted T-cell antigens," Trends Immunol, 22(11):583-588.

Lewis et al. (2010). "The Meningococcal Vaccine Candidate Neisserial Surface Protein A (Nspa) Binds to Factor H and Enhances Meningococcal Resistance to Complement," PLoS Pathog, 6(7):e1001027.

Maiden et al. (1998). "Multilocus sequence typing: a portable approach to the identification of clones within populations of pathogenic microorganisms," PNAS USA, 95(6):3140-3145.

Maksyutov et al. (1993). "ADEPT: a computer program for prediction of protein antigenic determinants," Comput Appl Biosci, 9(3):291-7.

Martin et al. (1997). "Highly conserved Neisseria meningitidis surface protein confers protection against experimental infection," J Exp Med., 185(7):1173-1183.

Masignani et al. (2003). "Vaccination against Neisseria meningitidis using three variants of the lipoprotein GNA1870," J Exp Med., 197(6):789-799.

Meister et al. (1995). "Two novel T cell epitope prediction algorithms based on MHC-binding motifs; comparison of predicted and

(56) References Cited

OTHER PUBLICATIONS published epitopes from *Mycobacterium tuberculosis* and HIV protein sequences," Vaccine, 13(6):581-91.

Oriente et al. (2010). "Expression of factor H binding protein of meningococcus responds to oxygen limitation through a dedicated FNR-regulated promoter," J Bacteriol, 192:691-701.

Pajon et al. (2012). "Design of Meningococcal Factor H Binding Protein Mutant Vaccines That Do Not Bind Human Complement Factor H," Infect Immun 80:2667-77.

Perkins-Balding et al. (2003). "Identification of funct

FIGURE 2
Figure 2A
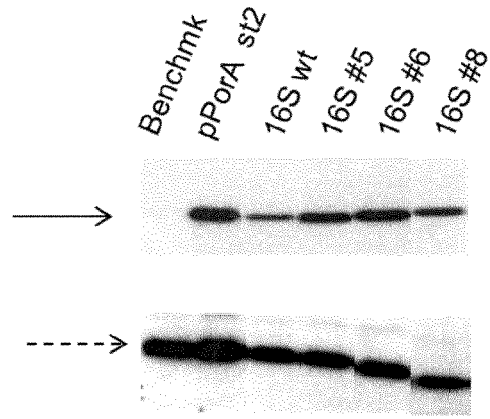
Figure 2B
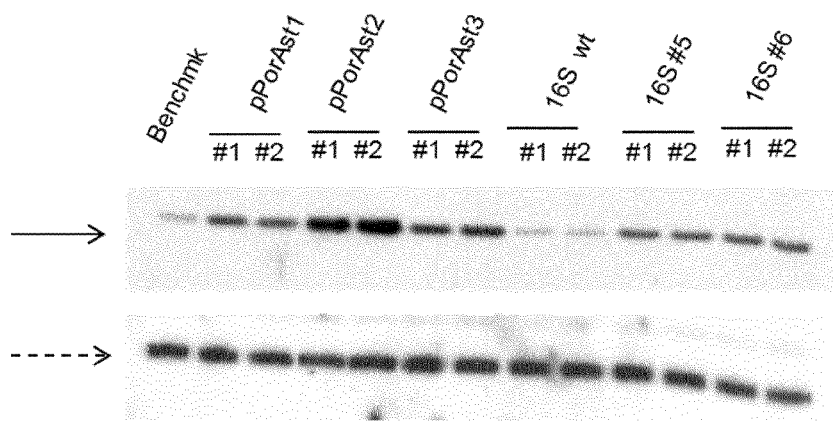
Figure 2C
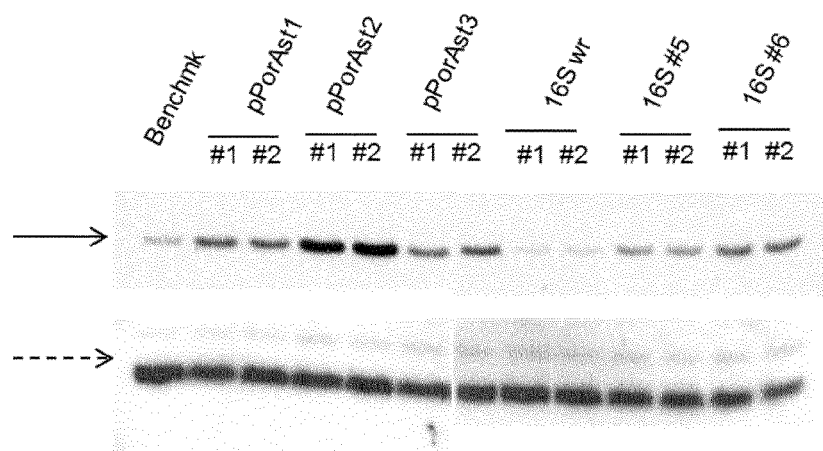

FIGURE 3
Figure 3A
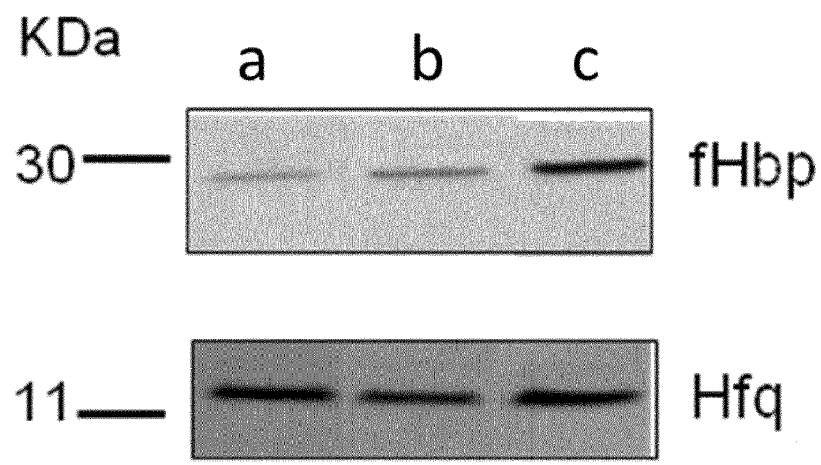
Figure 3B
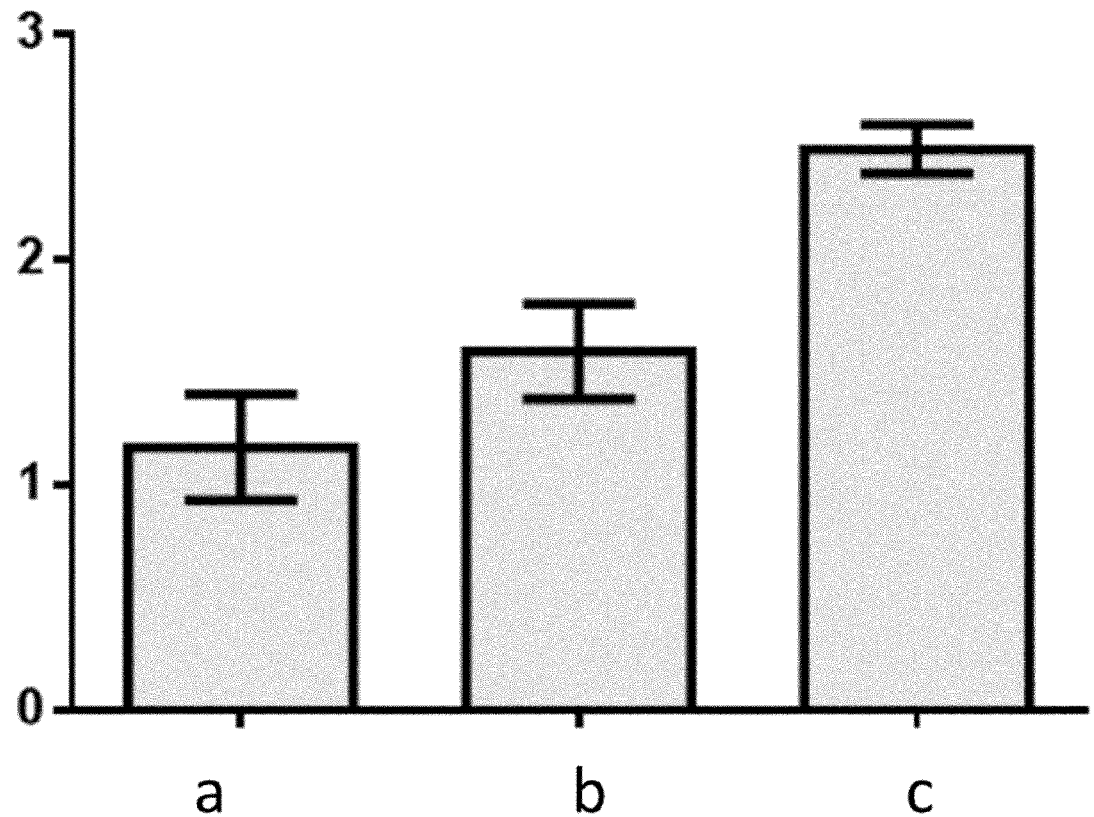

FIGURE 4
Figure 4A
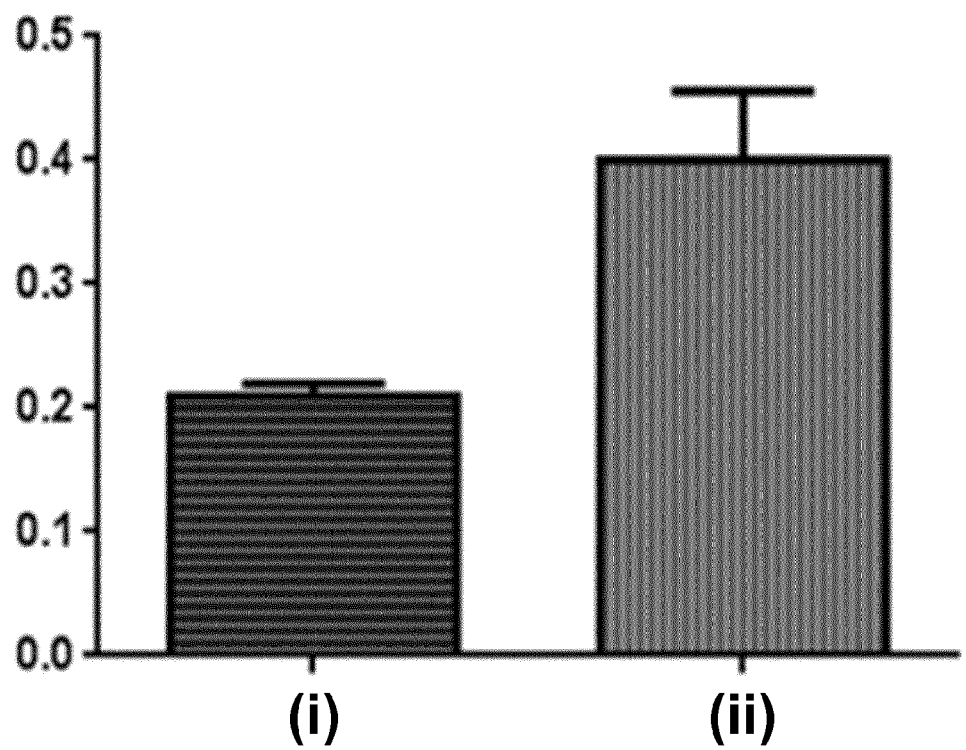
Figure 4B
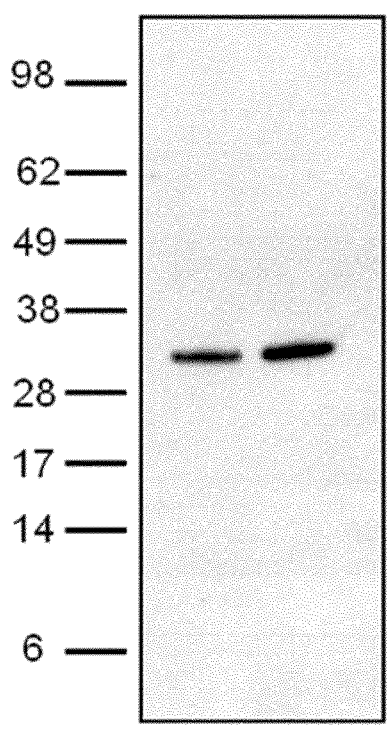

a b c d e

PROMOTERS FOR INCREASED PROTEIN EXPRESSION IN MENINGOCOCCUS

CROSS REFERENCE TO RELATED APPLICATIONS

This application is a U.S. National Phase of International Patent Application No. PCT/EP2013/052108 filed Feb. 1, 2013 and published in English, which claims the benefit of the U.S. provisional patent application No. 61/594,159, filed Feb. 2, 2012, the complete contents of which are incorporated herein by reference for all purposes.

SEQUENCE LISTING

The application includes a sequence listing that was filed with the PCT application as a part of the specification. The sequence listing is hereby incorporated by reference.

TECHNICAL FIELD

This invention is in the field of promoters for controlling transcription in meningococcal bacteria.

BACKGROUND ART

*Neisseria meningitidis* is a cause of bacterial meningitis. One approach to meningococcal vaccination relies on outer membrane vesicles (OMVs), as used in the Novartis MENZB™ product and the Norwegian Institute of Public Health MENBVAC™ product, both of which are generated by detergent treatment of meningococci.

It is known to change the protein composition of meningococcal outer membranes, and thus to change the composition of OMVs. Knockout of undesirable genes and over-expression of desirable genes have both been described. References 1-3 report pre-clinical studies of an OMV vaccine in which fHbp (also known as GNA1870) is over-expressed (and this over-expression can be combined with knockout of LpxL1 [4]). Reference 5 reported a clinical study of five formulations of an OMV vaccine in which PorA & FrpB are knocked-out and Hsf & TbpA are over-expressed. Reference 6 reports a phase I clinical study of a native outer membrane vesicle vaccine prepared from bacteria having inactivated synX and lpxL1 genes, over-expressed fHbp, two different PorA proteins and stabilised OpcA expression. Reference 7 reports a trivalent native outer membrane vesicle vaccine prepared from bacteria having inactivated synX and lpxL1 genes (and, in two cases, inactivated lgtA), two different PorA proteins, and over-expressed NadA or fHbp. Inactivation of genes such as lpxL1 is important if vesicles will be generated by methods which do not remove LPS.

These changes in protein composition can be effected in various ways. For instance, the bacteria can be growing under iron-limiting conditions in order to stimulate the expression of certain proteins related to iron metabolism. Other techniques can involve engineering the bacteria. For instance, reference 8 suggests that strong promoters (such as the porA, porB, lgtF, or hpuAB promoters) might be used to up-regulate expression of protective outer membrane proteins, or that suppressive transcription control mechanisms might be removed. Reference 9 suggests that genes can be engineered to remove their phase variability. The porA promoter was used in reference 7 to over-express NadA, whereas fHbp was over-expressed using the tac promoter.

It is an object of the invention to provide further and improved ways of modifying protein expression in meningococci, and in particular to provide promoters for driving expression of genes of interest. Up-regulation can be used to increase the levels of useful proteins in OMVs.

DISCLOSURE OF THE INVENTION

A first aspect of the invention uses modified porA promoters to drive transcription. The natural porA promoter, as used in examples 10-16 of reference 8, contains a poly-G sequence between its −35 and −10 regions, but this sequence can cause phase variation and so expression from the natural porA promoter can be unstable. The modified porA promoters of the invention are improved because they lack the wild-type poly-G sequence.

Thus the invention provides a nucleic acid comprising a promoter which includes
  (i) a −10 region from a meningococcal porA gene promoter and/or
  (ii) a −35 region from a meningococcal porA gene promoter,
wherein the −10 region and the −35 region are separated by an intervening (or spacer) sequence of 12-20 nucleotides, and wherein the intervening sequence either contains no poly-guanidine sequence or includes a poly-guanidine sequence having no more than eight consecutive guanidine nucleotides.

A second aspect of the invention uses promoters from a meningococcal rRNA-coding gene (such as the 16S rRNA gene) to drive transcription of a protein-coding gene. Thus the invention also provides a nucleic acid comprising a promoter operably linked to a downstream protein-coding gene, wherein the promoter includes (i) a −10 region from a meningococcal rRNA gene promoter and/or (ii) a −35 region from a meningococcal rRNA gene promoter.

The invention also provides a nucleic acid comprising a promoter region from a rRNA gene promoter operably linked to a protein-coding gene having a 5' UTR which contains translational regulatory elements for expression of the protein. The promoter region can include (i) a −10 region from a meningococcal rRNA gene promoter, (ii) a −35 region from a meningococcal rRNA gene promoter, and (iii) a 5' UTR from a gene such as the porA gene.

The invention also provides a nucleic acid comprising a promoter which includes SEQ ID NO: 18, or a variant of SEQ ID NO: 18 which differs from SEQ ID NO: 18 by up to 4 (i.e. 1, 2, 3, or 4) single-nucleotide insertions, deletions or substitutions.

The porA and rRNA promoters can be used in hybrid form, for instance to have a −10 region from a porA promoter and a −35 region from a rRNA promoter (which can be a consensus −35 region). Thus the invention also provides a nucleic acid comprising a promoter which includes either
  (i) a −10 region from a meningococcal rRNA gene and a −35 region from a meningococcal porA gene, or
  (ii) a −10 region from a meningococcal porA gene and a −35 region from a meningococcal rRNA gene.

The nucleic acids of the invention can be present in a bacterium, and in particular in a meningococcus. The promoters can drive expression of downstream protein-coding genes (in particular, genes encoding outer membrane proteins) to which they are operably linked, and the bacteria can be used to prepare vaccines (in particular vesicle-based vaccines). The invention also provides these bacteria, these vesicles, and these vaccines.

Promoters of the Invention

The two essential sequences in bacterial promoters are the −10 region (also known as the Pribnow box) and the −35 region. These are separated by an intervening sequence, and between the −10 region and the transcription start site (+1) is a short non-transcribed upstream sequence.

The PorA promoter has been studied in detail. Reference 10 reports a 6-mer −35 region, followed by a 16-mer of 17-mer intervening sequence, then a 7-mer Pribnow box, then a 7-mer non-transcribed upstream sequence, followed by transcribed nucleotide +1. The start codon in the wild-type porA gene is at nucleotide +59 of the transcript, and this 59-mer spacing was confirmed in reference 8.

Where a promoter of the invention includes a −10 region from a meningococcal porA gene promoter, this is typically a 6-mer TATAAT i.e. a typical −10 region 6-mer.

Where a promoter of the invention includes a −35 region from a meningococcal porA gene promoter, this is typically a 6-mer TGGTTT or ATGGTT.

The intervening sequence between a −35 region and a −10 region can be between 12-20 nucleotides e.g. 12, 13, 14, 15, 16, 17, 18, 19, or 20 nucleotides. An intervening sequence of 16, 17 or 18 nucleotides is typical.

The short non-transcribed upstream sequence is typically between 5-10 nucleotides e.g. 6, 7 or 8 nucleotides. It can be G:C-rich e.g. at least ½ of the nucleotides in the sequence are G or C e.g. at least 3 G/C residues in a 6-mer non-transcribed upstream sequence.

Thus a promoter can include a 6-mer −35 region, a 16-mer or 17-mer intervening sequence, a 6-mer −10 region, and a 6-mer or 7-mer non-transcribed upstream sequence, giving 34, 35 or 36 nucleotides of core promoter in total.

A promoter can, of course, continue upstream of the −35 region. Sequences upstream of the −35 region can be important for high-level expression from the promoter, of for regulation of expression from the promoters. For instance, in rRNA promoters sequences upstream of the core promoter called UP-elements can account for their exceptional strength increasing transcription as much as 300-fold [11, 12]. These can be recognised by the α-subunit of the RNA polymerase core. Thus a promoter of the invention can include an upstream UP-element, which will usually be A:T-rich. Similarly, a promoter of the invention can include an upstream CREN (contact regulatory element of Neisseria) [13].

Where a promoter of the invention includes a −35 region and/or a −10 region from a porA gene promoter, the short non-transcribed upstream sequence can be TGAAGAC.

Where a promoter of the invention includes a −35 region and/or a −10 region from a porA gene promoter, the intervening sequence can be varied, as shown in the examples. For instance, it can be TTTGCGGGGGGGGGGG (wild-type 16-mer; SEQ ID NO: 26) or TTTGCGGGGGGGGGGGGG (wild-type 18-mer; SEQ ID NO: 17) but these wild-type sequences are not preferred. Rather, the 11-mer or 13-mer poly-G sequence in this 16-mer or 18-mer can be interrupted by non-G nucleotide(s). Two preferred intervening sequences are TTTGCGAGGGAGGTGG (16-mer; SEQ ID NO: 27) and TTTTGCGAGGGAGGTGG (17-mer; SEQ ID NO: 28).

In some embodiments the intervening sequence contains no poly-guanidine sequence i.e. there is no GG dinucleotide within the intervening sequence. In other embodiments the intervening sequence can contain a poly-guanidine sequence, but it contains no more than eight consecutive guanidine nucleotides i.e. it does not include a sequence GGGGGGGG. Ideally, the intervening sequence does not include a sequence GGGGGGG. Ideally, the intervening sequence does not include a sequence GGGGGG. Ideally, the intervening sequence does not include a sequence GGGGG. Ideally, the intervening sequence does not include a sequence GGGG. The intervening sequence can include a GGG trinucleotide or a GG dinucleotide. Thus a poly-G sequence within the intervening sequence would extend for no more than 8 nucleotides in total, and ideally has no more than three consecutive guanidine residues.

Where a promoter of the invention includes a −10 region from a meningococcal rRNA gene promoter, this is typically a 6-mer TATAAT i.e. a typical −10 region 6-mer.

Where a promoter of the invention includes a −35 region from a meningococcal rRNA gene promoter, this is typically a 6-mer TTGACA (which is a consensus −35 region).

Where a promoter of the invention includes a −35 region and/or a −10 region from a meningococcal rRNA gene promoter, the intervening sequence can be GGCG-GAAGGAATACTT (SEQ ID NO: 29).

Where a promoter of the invention includes a −35 region and/or a −10 region from a rRNA gene promoter, the short non-transcribed upstream sequence can be TCGCAAC.

The porA and rRNA promoters can be used in hybrid form, and a useful promoter includes a −35 region from a rRNA gene (e.g. TTGACA), an intervening sequence modified from a porA gene (e.g. TTTGCGAGGGAGGTGG; SEQ ID NO: 27), a typical Pribnow box (TATAAT) and a short non-transcribed upstream sequence from a porA gene (e.g. TGAAGAC). Thus the promoter can include SEQ ID NO: 30 (TTGACATTTGCGAGGGAGGTGGTATAATTGAAGAC).

In some embodiments the promoter includes SEQ ID NO: 18 (a 35-mer fragment immediately before the transcription start site of the wild-type meningococcal 16S rRNA promoter). This sequence can be modified by 1, 2, 3, or 4 single-nucleotide insertions, deletions or substitutions within the 35-mer, as shown herein.

When present in functioning DNA form within a bacterium these promoters are operably linked to a sequence which encodes a protein of interest, whose transcription is controlled by the promoter. The invention can be used to express any protein of interest, but the protein is advantageously an outer membrane protein which can be retained in vesicles. Suitable examples of outer membrane proteins are given below, but the invention is preferably not used to drive expression of a transcript which encodes a PorA outer membrane protein.

In a coding DNA sequence, downstream of a promoter of the invention the DNA includes a transcription start site, followed by a 5' untranslated region (typically including a Shine-Dalgarno sequence) and then a start codon for the encoded protein of interest.

Where the promoter is from a rRNA gene, the start of the transcribed sequence is ideally derived from a protein-coding gene rather than from a rRNA gene. Thus the rRNA promoter (e.g. SEQ ID NO: 18 or variants) can be fused to the 5' UTR from a meningococcal protein-coding gene. In some embodiments, the rRNA promoter is fused to the 5' UTR from a porA gene (a 58-mer), and this 5' UTR is then fused to the coding sequence of a gene of interest. The 5' UTR should include translational regulatory elements which permit translation of protein from the protein-coding gene. Thus this embodiment uses the rRNA promoter to produce a protein-coding transcript which can be translated. Sequences downstream of the promoter, inside the 5' UTR, may be important for regulation of transcription or post-transcriptional effects on expression of downstream genes.

The 5' UTR of a porA gene can also be used with a modified porA promoter of the invention, such that the modified porA promoter is linked to a 5' UTR from a porA gene, which is then fused to the coding sequence for a protein of interest.

A useful porA 5' UTR can include the nucleotide sequence of SEQ ID NO: 39, namely GTATCGGGTGTTTGC-CCGATGTTTTTAGGTTTTTATCAAATTTA-CAAAAGGAAGCC, or a sequence which differs from SEQ ID NO: 39 by up to 5 (i.e. 1, 2, 3, 4, or 5) single-nucleotide insertions, deletions or substitutions.

It will be appreciated that discussions of promoter sequences herein refer to the sense strand. In double-stranded DNA, from which transcription takes place, the promoter has a complementary strand. Where two promoter elements are said to be separated by 'n' nucleotides, this is again a reference to the number of nucleotides in the sense strand; in double-stranded DNA the element will be separated by 'n' base pairs. If a promoter element is said to lack a guanidine residue, this is again a reference to the sense strand; in double-stranded DNA, for example, a guanidine-free promoter could include a guanidine residue, but only as a complementary base in the antisense strand for a cytosine residue in the sense strand. Although the invention is described by reference to the sense strand, the scope of the invention includes double-stranded nucleic acids including such sense strands, as well as single-stranded nucleic acids including such sense strands or including antisense forms of these sense strands (these antisense strands can, of course, be used to prepare the sense strands, by standard techniques).

Vesicles

The invention is particularly useful when preparing meningococcal vesicles i.e. any proteoliposomic vesicle obtained by disruption of or blebbing from a meningococcal outer membrane to form vesicles therefrom that retain antigens from the outer membrane. Thus the term includes, for instance, OMVs (sometimes referred to as 'blebs'), microvesicles (MVs [14]) and 'native OMVs' ('NOMVs' [15]).

MVs and NOMVs are naturally-occurring membrane vesicles that form spontaneously during bacterial growth and are released into culture medium. MVs can be obtained by culturing Neisseria in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture e.g. refs. 16 & 17 describe Neisseria with high MV production.

Another useful technique for spontaneous outer membrane vesicle production is to inactivate the mltA gene in a meningococcus, as disclosed in reference 18. These mutant bacteria release vesicles into their culture medium during growth.

OMVs are prepared artificially from bacteria, and may be prepared using detergent treatment (e.g. with deoxycholate), or by non-detergent means (e.g. see reference 19). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [20 & 21] being preferred for treating Neisseria) at a pH sufficiently high not to precipitate the detergent [22]. Other techniques may be performed substantially in the absence of detergent [19] using techniques such as sonication, homogenisation, microfluidisation, cavitation, osmotic shock, grinding, French press, blending, etc. Methods using no or low detergent can retain useful antigens such as NspA [19]. Thus a method may use an OMV extraction buffer with about 0.5% deoxycholate or lower e.g. about 0.2%, about 0.1%, <0.05% or zero. A useful process for OMV preparation is described in reference 23 and involves ultrafiltration on crude OMVs, rather than instead of high speed centrifugation. The process may involve a step of ultracentrifugation after the ultrafiltration takes place.

A convenient way of purifying vesicles is the dual filtration method disclosed in reference 24.

Preferred vesicles are those which form spontaneously during bacterial culture, rather than those which are released only after physical or chemical treatment of the bacteria. Growth of meningococci having an inactivated MltA is a preferred way of producing vesicles in this way. Reference 47 discloses other ways of producing hyperblebbing strains. For spontaneously-released vesicles it is preferable to use bacteria which do not produce intact LOS (detergent-extracted vesicles have reduced levels of potentially reactogenic LOS).

If lipo-oligosaccharide (LOS) is present in a vesicle it is possible to treat the vesicle so as to link its LOS and protein components ("intra-bleb" conjugation [48]).

The vesicles may lack LOS altogether, or they may lack hexa-acylated LOS e.g. LOS in the vesicles may have a reduced number of secondary acyl chains per LOS molecule [25]. For example, the vesicles may from a strain which has a lpxL1 deletion or mutation which results in production of a penta-acylated LOS [2,43]. LOS in a strain may lack a lacto-N-neotetraose epitope e.g. it may be a 1st and/or lgtB knockout strain [5]. LOS may lack at least one wild-type primary O-linked fatty acid [26]. The LOS may have no a chain. The LOS may comprise GlcNAc-$Hep_2$phosphoethanolamine-$KDO_2$-Lipid A [27].

The vesicles may include one, more than one, or (preferably) zero PorA serosubtypes. Modification of meningococcus to provide multi-PorA OMVs is known e.g. from reference 28, which discloses the construction of vesicles from strains modified to express six different PorA subtypes, and from reference 29. Conversely, modification to remove PorA is also known e.g. from reference 5.

The vesicles may be free from one of both of PorA and FrpB. Preferred vesicles are PorA-free.

The vesicles may lack capsular saccharide. For instance they may be derived from a strain that has one or more of the genes for capsule biosynthesis and/or export deactivated (e.g. synX).

The invention may be used with mixtures of vesicles from different strains. For instance, reference 30 discloses vaccine comprising multivalent meningococcal vesicle compositions, comprising a first vesicle derived from a meningococcal strain with a serosubtype prevalent in a country of use, and a second vesicle derived from a strain that need not have a serosubtype prevent in a country of use. Reference 31 also discloses useful combinations of different vesicles. A combination of vesicles from strains in each of the L2 and L3 immunotypes may be used in some embodiments.

Over-Expression

Promoters of the invention can be used to over-express a gene of interest in meningococcus. Where the gene encodes an outer membrane protein antigen, this over-expression can be used to provide a vesicle which advantageously retains that antigen. Such vesicles are discussed in more detail below. As a result of the over-expression, vesicles prepared from the modified meningococcus contain higher levels of the over-expressed antigen(s) than seen in a corresponding wild-type meningococcus. The increase in expression in the vesicles is usefully at least 10%, measured in mass of the relevant antigen per unit mass of vesicles, and is more usefully at least 20%, 30%, 40%, 50%, 75%, 100% or more.

Suitable recombinant modifications which can be used to over-express an antigen by using promoters of the invention include, but are not limited to: (i) promoter replacement; (ii) gene addition; and/or (iii) gene replacement. These three techniques can, if desired, be used in conjunction with (iv) repressor knockout.

In promoter replacement, the promoter which controls expression of the antigen's gene in a bacterium is replaced with a promoter of the invention in order to provide higher levels of expression.

In gene addition, a bacterium which already expresses the antigen receives a second copy of the relevant gene. This second copy can be integrated into the bacterial chromosome or can be on an episomal element such as a plasmid. The second copy can be expressed using a promoter of the invention. The effect of the gene addition is to increase the amount of expressed antigen. Where a plasmid is used, it is ideally a plasmid with a high copy number e.g. above 10, or even above 100.

In gene replacement, gene addition occurs but is accompanied by deletion of the existing copy of the gene. For instance, this approach was used in reference 3, where a bacterium's endogenous chromosomal fHbp gene was deleted and replaced by a plasmid-encoded copy (see also reference 32). Expression from the replacement copy, using a promoter of the invention, is higher than from the previous copy, thus leading to over-expression.

In some embodiments gene replacement occurs where gene addition is accompanied by the deletion of another gene. For instance when the knocking out of an endogenous gene is required but is not the gene of interest that is being overexpressed by the promoter of the invention.

In some embodiments, more than one event of gene addition or gene replacement may occur such that expression from multiple copies of the gene of interest by promoters of the invention or combinations of overexpression of different genes of interest by promoters of the invention may take place.

Over-expression of at least one antigen will use a promoter of the invention, but these promoters can be used in conjunction with other techniques. For instance, the promoters can be used in conjunction with repressor knockout, in which a protein which represses expression of an antigen of interest is knocked out. This knockout means that the repression does not occur and the antigen of interest can be expressed at a higher level.

For instance, where NadA is over-expressed, the nadA gene can use a promoter of the invention, but in addition the gene encoding NadR (NMB1843) can be deleted. NadR a transcriptional repressor protein [33] which down-regulates or represses the NadA-encoding gene in all strains tested. Knockout of NadR results in constitutive expression of NadA. An alternative way to over-express NadA is to add 4-hydroxyphenylacetic to the culture medium. Thus promoters of the invention can be used as an over-expression strategy alone, or in combination with other approaches.

In some embodiments a bacterium over-expresses NadA.
In some embodiments a bacterium over-expresses NHBA.
In some embodiments a bacterium over-expresses fHbp.

In some embodiments, a bacterium over-expresses both NHBA and NadA.

In some embodiments, a bacterium over-expresses both fHbp and NadA.

In some embodiments, a bacterium over-expresses both fHbp and NHBA.

In some embodiments, a bacterium over-expresses fHbp, NHBA and NadA.

In addition to over-expressing NHBA and/or NadA, a bacterium may over-express one or more further antigens. For instance, a bacterium may over-express one or more of: (a) NhhA; (b) TbpA; (c) HmbR; (d) TbpB; (e) NspA; (f) Cu,Zn-superoxide dismutase; (g) Omp85; (h) App; and/or (i) fHbp. Over-expression of NhhA is already reported in references 5 and 34. Over-expression of TbpA is already reported in references 5, 34 and 35. Over-expression of HmbR is already reported in reference 36. Over-expression of TbpB is already reported in reference 35. Over-expression of NspA is already reported in reference 37, in combination with porA and cps knockout. Over-expression of Cu,Zn-superoxide dismutase is already reported in reference 35. Over-expression of fHbp is already reported in references 1-3 & 32, and by a different approach (expressing a constitutively-active mutant FNR) in references 38 & 39. Where more than one antigen is over-expressed, at least one antigen will be over-expressed using a promoter of the invention, and in some embodiments more than one antigen will be over-expressed using a promoter of the invention.

In some embodiments a bacterium over-expresses NHBA, NadA and fHbp. These three antigens are components of the "universal vaccine" disclosed in reference 40 or "4CMenB" [41,42]. In one embodiment, expression of NHBA is controlled by a promoter of the invention, NadR is knocked out, and the strain expresses a constitutively active mutant FNR. In another embodiment, expression of NHBA is controlled by a promoter of the invention, expression of fHbp is controlled by a promoter of the invention, and NadR is knocked out.

An over-expressing modified strain will generally be isogenic with its parent strain, except for a genetic modification. As a result of the modification, expression of the antigen of interest in the modified strain is higher (under the same conditions) than in the parent strain.

Bacteria

As mentioned above, vesicles of the invention are prepared from meningococci which over-express the relevant antigen(s) due to genetic modification, involving at least the use of a promoter of the invention. The invention also provides these bacteria. They can be used for preparing vesicles of the invention.

In addition to including a promoter of the invention, the meningococci may include one or more further modifications. For instance, it can have a knockout of one or more of lpxL1, lgtA, lgtB, porA, frpB, synX, mltA and/or 1st. For instance, reference 43 reports a NOMV vaccine prepared from bacteria having inactivated synX, lpxL1, and lgtA genes. Knockout of at least lpxL1 and synX is particularly useful.

The bacterium may have low endotoxin levels, achieved by knockout of enzymes involved in LPS biosynthesis [44,45].

The bacterium may be from any serogroup e.g. A, B, C, W135, or Y. It is preferably serogroup B or serogroup W135.

The bacterium may be of any serotype (e.g. 1, 2a, 2b, 4, 14, 15, 16, etc.), any serosubtype, and any immunotype (e.g. L1; L2; L3; L3,3,7; L10; etc.). Vesicles can usefully be prepared from strains having one of the following subtypes:

P1.2; P1.2,5; P1.4; P1.5; P1.5,2; P1.5,c; P1.5c,10; P1.7,16; P1.7,16b; P1.7h,4; P1.9; P1.15; P1.9,15; P1.12,13; P1.13; P1.14; P1.21,16; P1.22,14.

The bacterium may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3. These lineages have been defined by multilocus enzyme electrophoresis (MLEE), but multilocus sequence typing (MLST) has also been used to classify meningococci [ref. 46] e.g. the ET-37 complex is the ST-11 complex by MLST, the ET-5 complex is ST-32 (ET-5), lineage 3 is ST-41/44, etc.

In some embodiments a bacterium may include one or more of the knockout and/or over-expression mutations disclosed in references 8, 37, 47 and 48. Suitable genes for modification include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB [8]; (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB; (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB; and (d) CtrA, CtrB, CtrD, FrpB, OpA, OpC, PilC, PorB, SiaD, SynA, SynB, and/or SynC.

As mentioned above, the meningococcus advantageously does not express an active MltA (GNA33), such that it spontaneously releases vesicles e.g. which contain antigens which are expressed using a promoter of the invention.

Ideally, the bacterium does not express a native LPS e.g. it has a mutant or knockout of LpxL1 and/or of LgtB.

Where the bacterium has a knockout, it is convenient to achieve this knockout by insertion of a sequence including a promoter of the invention controlling transcription of a protein of interest. For example, the genomic synX or lpxL1 gene can be knocked out by inserting within it a sequence which includes a promoter of the invention which controls expression of an outer membrane protein such as fHbp. A single transformation event can thus be used to achieve two goals.

A bacterium of the invention may include a selection marker e.g. an antibiotic resistance marker.

A bacterium may have one or more, or all, of the following characteristics: (i) down-regulated or knocked-out LgtB and/or GalE to truncate the meningococcal LOS; (ii) up-regulated TbpA; (iii) up-regulated NhhA; (iv) up-regulated Omp85; (v) up-regulated LbpA; (vi) up-regulated NspA; (vii) knocked-out PorA; (viii) down-regulated or knocked-out FrpB; (ix) down-regulated or knocked-out Opa; (x) down-regulated or knocked-out Opc; (xii) deleted cps gene complex. A truncated LOS can be one that does not include a sialyl-lacto-N-neotetraose epitope e.g. it might be a galactose-deficient LOS. The LOS may have no a chain.

A bacterium may have one or more, or all, of the following characteristics: (i) down-regulated or knocked-out LgtA; (ii) down-regulated or knocked-out LpxL1; (iii) down-regulated or knocked-out SynX; (iv) more than one PorA subtype, such as two different PorA subtypes; and/or (v) an up-regulated outer membrane antigen, such as NadA or fHbp.

Strain Production

The invention provides a process for preparing a meningococcal strain suitable for vesicle preparation, comprising steps of (i) choosing a starting strain which expresses a first amount of an antigen when grown in specific culture conditions, then (ii) modifying the starting strain to provide a modified strain including a promoter of the invention, wherein the modified strain expresses a second amount of the antigen when grown in the same specific culture conditions, the second amount being higher than the first amount. The second amount is usefully at least 10%, higher than the first amount, measured in mass of the relevant antigen per unit mass of bacteria, and is more usefully at least 20%, 30%, 40%, 50%, 75%, 100% or more.

This process can be followed by a step of (iii) culturing the modified bacteria obtained in step (ii) to provide a bacterial culture.

The process can also involve further steps of genetic manipulation, either before or after the introduction of a promoter of the invention. A promoter of the invention can be introduced into the bacterium more than once, and at more than one site e.g. with multiple controlled genes.

The invention also provides a process for preparing a meningococcal vesicle, comprising a step of treating a bacterial culture obtained by a process of the invention (as described above) such that its outer membrane forms vesicles. This treatment step can use any of the techniques discussed above.

The invention also provides a process for preparing a meningococcal vesicle, comprising a step of treating a meningococcus of the invention such that its outer membrane forms vesicles. This treatment step can use any of the techniques discussed above.

The invention also provides a process for preparing a meningococcal vesicle, comprising a step of culturing a meningococcus of the invention under conditions in which its outer membrane spontaneously sheds vesicles. For instance, the meningococcus might not express active MltA.

Useful starting strains are in meningococcus serogroup B. Three useful starting meningococcal strains for preparing bacteria which over-express an antigen of interest are MC58, NZ98/254, and H44/76. MC58 has PorA serosubtype 1.7,16; NZ98/254 has serosubtype P1.7-2,4; and H44/76 has serosubtype 1.7,16. Other strains with these serosubtypes can also be used.

Vectors Etc.

The invention provides promoters as described above. These can be present in a bacterial chromosome, or in an extra-chromosomal or episomal nucleic acid e.g. within a plasmid. A bacterium can include 1 or more copies of the promoter of the invention. Where a bacterium includes 2 copies, these can be in the chromosome and/or episome(s).

Thus the invention provides a bacterium comprising (i) a chromosome including at least one promoter of the invention and/or (ii) an episome, such as a plasmid, including at least one promoter of the invention.

The invention also provides a nucleic acid vector comprising a promoter of the invention, such as a bacterial expression vector.

These promoters within these vectors or bacteria can be 'orphan' promoters without any downstream transcribable sequence, but they will typically be operably linked to a sequence which is transcribed, and which is then translated to express a protein of interest.

Antigens

NHBA (Neisserial Heparin Binding Antigen)

NHBA [51] was included in the published genome sequence for meningococcal serogroup B strain MC58 [78] as gene NMB2132 (GenBank accession number GI:7227388; SEQ ID NO: 9 herein). Sequences of NHBA from many strains have been published since then. For example, allelic forms of NHBA (referred to as protein '287') can be seen in FIGS. 5 and 15 of reference 49, and in example 13 and FIG. 21 of reference 50 (SEQ IDs 3179 to 3184 therein). Various immunogenic fragments of NHBA have also been reported.

Preferred NHBA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9; and/or (b) comprising a fragment of at least 'n' consecutive amino acids of SEQ ID NO: 9, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 9.

The most useful NHBA antigens can elicit antibodies which, after administration to a subject, can bind to a meningococcal polypeptide consisting of amino acid sequence SEQ ID NO: 9. Advantageous NHBA antigens for use with the invention can elicit bactericidal anti-meningococcal antibodies after administration to a subject.

Over-expression of NHBA has previously been achieved in various ways e.g. introduction of a NHBA gene under the control of an IPTG-inducible promoter [51].

NadA (Neisserial Adhesin A)

The NadA antigen was included in the published genome sequence for meningococcal serogroup B strain MC58 [78] as gene NMB1994 (GenBank accession number GI:7227256; SEQ ID NO: 10 herein). The sequences of NadA antigen from many strains have been published since then, and the protein's activity as a Neisserial adhesin has been well documented. Various immunogenic fragments of NadA have also been reported.

Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 10.

The most useful NadA antigens can elicit antibodies which, after administration to a subject, can bind to a meningococcal polypeptide consisting of amino acid sequence SEQ ID NO: 10. Advantageous NadA antigens for use with the invention can elicit bactericidal anti-meningococcal antibodies after administration to a subject. SEQ ID NO: 6 is one such fragment.

HmbR

The full-length HmbR sequence was included in the published genome sequence for meningococcal serogroup B strain MC58 [78] as gene NMB1668 (SEQ ID NO: 7 herein). Reference 52 reports a HmbR sequence from a different strain (SEQ ID NO: 8 herein), and reference 36 reports a further sequence (SEQ ID NO: 19 herein). SEQ ID NOs: 7 and 8 differ in length by 1 amino acid and have 94.2% identity. SEQ ID NO: 19 is one amino acid shorter than SEQ ID NO: 7 and they have 99% identity (one insertion, seven differences) by CLUSTALW. The invention can use any such HmbR polypeptide.

The invention can use a polypeptide that comprises a full-length HmbR sequence, but it will often use a polypeptide that comprises a partial HmbR sequence. Thus in some embodiments a HmbR sequence used according to the invention may comprise an amino acid sequence having at least i % sequence identity to SEQ ID NO: 7, where the value of i is 50, 60, 70, 80, 90, 95, 99 or more. In other embodiments a HmbR sequence used according to the invention may comprise a fragment of at least j consecutive amino acids from SEQ ID NO: 7, where the value of j is 7, 8, 10, 12, 14, 16, 18, 20, 25, 30, 35, 40, 50, 60, 70, 80, 90, 100, 150, 200, 250 or more. In other embodiments a HmbR sequence used according to the invention may comprise an amino acid sequence (i) having at least i % sequence identity to SEQ ID NO: 7 and/or (ii) comprising a fragment of at least j consecutive amino acids from SEQ ID NO: 7.

Preferred fragments of j amino acids comprise an epitope from SEQ ID NO: 7. Such epitopes will usually comprise amino acids that are located on the surface of HmbR. Useful epitopes include those with amino acids involved in HmbR's binding to haemoglobin, as antibodies that bind to these epitopes can block the ability of a bacterium to bind to host haemoglobin. The topology of HmbR, and its critical functional residues, were investigated in reference 53. Fragments that retain a transmembrane sequence are useful, because they can be displayed on the bacterial surface e.g. in vesicles. Examples of long fragments of HmbR correspond to SEQ ID NOs: 21 and 22. If soluble HmbR is used, however, sequences omitting the transmembrane sequence, but typically retaining epitope(s) from the extracellular portion, can be used.

The most useful HmbR antigens can elicit antibodies which, after administration to a subject, can bind to a meningococcal polypeptide consisting of amino acid sequence SEQ ID NO: 7. Advantageous HmbR antigens for use with the invention can elicit bactericidal anti-meningococcal antibodies after administration to a subject.

fHbp (Factor H Binding Protein)

The fHbp antigen has been characterised in detail. It has also been known as protein '741' [SEQ IDs 2535 & 2536 in ref. 50], 'NMB1870', 'GNA1870' [54-56], 'P2086', 'LP2086' or 'ORF2086' [57-59]. It is naturally a lipoprotein and is expressed across all meningococcal serogroups. The structure of fHbp's C-terminal immunodominant domain ('fHbpC') has been determined by NMR [60]. This part of the protein forms an eight-stranded β-barrel, whose strands are connected by loops of variable lengths. The barrel is preceded by a short α-helix and by a flexible N-terminal tail.

The fHbp antigen falls into three distinct variants [61] and it has been found that serum raised against a given family is bactericidal within the same family, but is not active against strains which express one of the other two families i.e. there is intra-family cross-protection, but not inter-family cross-protection. The invention can use a single fHbp variant, but is will usefully include a fHbp from two or three of the variants. Thus it may use a combination of two or three different fHbps, selected from: (a) a first protein, comprising an amino acid sequence having at least a % sequence identity to SEQ ID NO: 1 and/or comprising an amino acid sequence consisting of a fragment of at least x contiguous amino acids from SEQ ID NO: 1; (b) a second protein, comprising an amino acid sequence having at least b % sequence identity to SEQ ID NO: 2 and/or comprising an amino acid sequence consisting of a fragment of at least y contiguous amino acids from SEQ ID NO: 2; and/or (c) a third protein, comprising an amino acid sequence having at least c % sequence identity to SEQ ID NO: 3 and/or comprising an amino acid sequence consisting of a fragment of at least z contiguous amino acids from SEQ ID NO: 3.

The value of a is at least 85 e.g. 86, 87, 88, 89, 90, 91, 92, 93, 94, 95, 96, 97, 98, 99, 99.5, or more.

The value of b is at least 85 e.g. 86, 87, 88, 89, 90, 91, 92, 93, 94, 95, 96, 97, 98, 99, 99.5, or more.

The value of c is at least 85 e.g. 86, 87, 88, 89, 90, 91, 92, 93, 94, 95, 96, 97, 98, 99, 99.5, or more.

The values of a, b and c are not intrinsically related to each other.

The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other.

Where the invention uses a single fHbp variant, a composition may include a polypeptide comprising (a) an amino acid sequence having at least a % sequence identity to SEQ ID NO: 1 and/or comprising an amino acid sequence consisting of a fragment of at least x contiguous amino acids from SEQ ID NO: 1; or (b) an amino acid sequence having at least b % sequence identity to SEQ ID NO: 2 and/or comprising an amino acid sequence consisting of a fragment of at least y contiguous amino acids from SEQ ID NO: 2; or (c) an amino acid sequence having at least c % sequence identity to SEQ ID NO: 3 and/or comprising an amino acid sequence consisting of a fragment of at least z contiguous amino acids from SEQ ID NO: 3.

Where the invention uses a fHbp from two or three of the variants, a composition may include a combination of two or three different fHbps selected from: (a) a first polypeptide, comprising an amino acid sequence having at least a % sequence identity to SEQ ID NO: 1 and/or comprising an amino acid sequence consisting of a fragment of at least x contiguous amino acids from SEQ ID NO: 1; (b) a second polypeptide, comprising an amino acid sequence having at least b % sequence identity to SEQ ID NO: 2 and/or comprising an amino acid sequence consisting of a fragment of at least y contiguous amino acids from SEQ ID NO: 2; and/or (c) a third polypeptide, comprising an amino acid sequence having at least c % sequence identity to SEQ ID NO: 3 and/or comprising an amino acid sequence consisting of a fragment of at least z contiguous amino acids from SEQ ID NO: 3. The first, second and third polypeptides have different amino acid sequences.

Where the invention uses a fHbp from two of the variants, a composition can include both: (a) a first polypeptide, comprising an amino acid sequence having at least a % sequence identity to SEQ ID NO: 1 and/or comprising an amino acid sequence consisting of a fragment of at least x contiguous amino acids from SEQ ID NO: 1; and (b) a second polypeptide, comprising an amino acid sequence having at least b % sequence identity to SEQ ID NO: 2 and/or comprising an amino acid sequence consisting of a fragment of at least y contiguous amino acids from SEQ ID NO: 2. The first and second polypeptides have different amino acid sequences.

Where the invention uses a fHbp from two of the variants, a composition can include both: (a) a first polypeptide, comprising an amino acid sequence having at least a % sequence identity to SEQ ID NO: 1 and/or comprising an amino acid sequence consisting of a fragment of at least x contiguous amino acids from SEQ ID NO: 1; (b) a second polypeptide, comprising an amino acid sequence having at least c % sequence identity to SEQ ID NO: 3 and/or comprising an amino acid sequence consisting of a fragment of at least z contiguous amino acids from SEQ ID NO: 3. The first and second polypeptides have different amino acid sequences.

Another useful fHbp which can be used according to the invention is one of the modified forms disclosed, for example, in reference 62 e.g. comprising SEQ ID NO: 20 or 23 therefrom. These modified forms can elicit antibody responses which are broadly bactericidal against meningococci. SEQ ID NO: 77 in reference 62 is another useful fHbp sequence which can be used.

A useful modification of fHbp, including of the sequences mentioned above, is a mutation which reduces or removes the protein's affinity for factor H. For instance, references 63 & 64 disclose such mutations at residues Glu-283 and/or Glu-304 by their numbering (subtract 72 from this numbering scheme to match SEQ ID NO: 1 herein). Similarly, references 65 & 66 discloses mutation (e.g. to Ser) at position Arg-41 by their numbering (subtract 7 to match SEQ ID NO: 1) for variant 1 and at positions 80, 211, 218, 220, 222, and/or 236 by their numbering (subtract 7 to match SEQ ID NO: 2) for variant 2. Alignments will quickly reveal the corresponding residues for any fHbp sequence of interest. The Arg-41-Ser mutation in variant 1 sequences is particularly preferred.

fHbp protein(s) in a OMV will usually be lipidated e.g. at a N-terminus cysteine. In other embodiments they will not be lipidated.

NspA (Neisserial Surface Protein A)

The NspA antigen was included in the published genome sequence for meningococcal serogroup B strain MC58 [78] as gene NMB0663 (GenBank accession number GI:7225888; SEQ ID NO: 11 herein). The antigen was previously known from references 67 & 68. The sequences of NspA antigen from many strains have been published since then. Various immunogenic fragments of NspA have also been reported.

Preferred NspA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 11.

The most useful NspA antigens can elicit antibodies which, after administration to a subject, can bind to a meningococcal polypeptide consisting of amino acid sequence SEQ ID NO: 11. Advantageous NspA antigens for use with the invention can elicit bactericidal anti-meningococcal antibodies after administration to a subject.

NhhA (*Neisseria* Hia Homologue)

The NhhA antigen was included in the published genome sequence for meningococcal serogroup B strain MC58 [78] as gene NMB0992 (GenBank accession number GI:7226232; SEQ ID NO: 12 herein). The sequences of NhhA antigen from many strains have been published since e.g. refs 49 & 69, and various immunogenic fragments of NhhA have been reported. It is also known as Hsf.

Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 12.

The most useful NhhA antigens can elicit antibodies which, after administration to a subject, can bind to a meningococcal polypeptide consisting of amino acid sequence SEQ ID NO: 12. Advantageous NhhA antigens for use with the invention can elicit bactericidal anti-meningococcal antibodies after administration to a subject.

App (Adhesion and Penetration Protein)

The App antigen was included in the published genome sequence for meningococcal serogroup B strain MC58 [78] as gene NMB1985 (GenBank accession number GI:7227246; SEQ ID NO: 13 herein). The sequences of App antigen from many strains have been published since then. It has also been known as 'ORF1' and 'Hap'. Various immunogenic fragments of App have also been reported.

Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 13.

The most useful App antigens can elicit antibodies which, after administration to a subject, can bind to a meningococcal polypeptide consisting of amino acid sequence SEQ ID NO: 13. Advantageous App antigens for use with the invention can elicit bactericidal anti-meningococcal antibodies after administration to a subject.

Omp85 (85 kDa Outer Membrane Protein)

The Omp85 antigen was included in the published genome sequence for meningococcal serogroup B strain MC58 [78] as gene NMB0182 (GenBank accession number GI:7225401; SEQ ID NO: 14 herein). The sequences of Omp85 antigen from many strains have been published since then. Further information on Omp85 can be found in references 70 and 71. Various immunogenic fragments of Omp85 have also been reported.

Preferred Omp85 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 14; and/or (b) comprising a fragment of at least 'n' consecutive amino acids of SEQ ID NO: 14, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 14.

The most useful Omp85 antigens can elicit antibodies which, after administration to a subject, can bind to a meningococcal polypeptide consisting of amino acid sequence SEQ ID NO: 14. Advantageous Omp85 antigens for use with the invention can elicit bactericidal anti-meningococcal antibodies after administration to a subject.

TbpA

The TbpA antigen was included in the published genome sequence for meningococcal serogroup B strain MC58 [78] as gene NMB0461 (GenBank accession number GI:7225687; SEQ ID NO: 23 herein). The sequences of TbpA from many strains have been published since then. Various immunogenic fragments of TbpA have also been reported.

Preferred TbpA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 23; and/or (b) comprising a fragment of at least 'n' consecutive amino acids of SEQ ID NO: 23, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 23.

The most useful TbpA antigens can elicit antibodies which, after administration to a subject, can bind to a meningococcal polypeptide consisting of amino acid sequence SEQ ID NO: 23. Advantageous TbpA antigens for use with the invention can elicit bactericidal anti-meningococcal antibodies after administration to a subject.

TbpB

The TbpB antigen was included in the published genome sequence for meningococcal serogroup B strain MC58 [78] as gene NMB1398 (GenBank accession number GI:7225686; SEQ ID NO: 24 herein). The sequences of TbpB from many strains have been published since then. Various immunogenic fragments of TbpB have also been reported.

Preferred TbpB antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 24; and/or (b) comprising a fragment of at least 'n' consecutive amino acids of SEQ ID NO: 24, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 24.

The most useful TbpB antigens can elicit antibodies which, after administration to a subject, can bind to a meningococcal polypeptide consisting of amino acid sequence SEQ ID NO: 24. Advantageous TbpB antigens for use with the invention can elicit bactericidal anti-meningococcal antibodies after administration to a subject.

Cu,Zn-Superoxide Dismutase

The Cu,Zn-superoxide dismutase antigen was included in the published genome sequence for meningococcal serogroup B strain MC58 [78] as gene NMB1398 (GenBank accession number GL7226637; SEQ ID NO: 25 herein). The sequences of Cu,Zn-superoxide dismutase from many strains have been published since then. Various immunogenic fragments of Cu,Zn-superoxide dismutase have also been reported.

Preferred Cu,Zn-superoxide dismutase antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 25; and/or (b) comprising a fragment of at least 'n' consecutive amino acids of SEQ ID NO: 25, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 25.

The most useful Cu,Zn-superoxide dismutase antigens can elicit antibodies which, after administration to a subject, can bind to a meningococcal polypeptide consisting of amino acid sequence SEQ ID NO: 25. Advantageous Cu,Zn-superoxide dismutase antigens for use with the invention can elicit bactericidal anti-meningococcal antibodies after administration to a subject.

Pharmaceutical Compositions

Vesicles of the invention are useful as active ingredients in immunogenic pharmaceutical compositions for administration to a patient. These will typically include a pharmaceutically acceptable carrier, and a thorough discussion of such carriers is available in reference 72.

Effective dosage volumes can be routinely established, but a typical human dose of the composition has a volume of about 0.5 ml e.g. for intramuscular injection. The RIVM OMV-based vaccine was administered in a 0.5 ml volume [73] by intramuscular injection to the thigh or upper arm. MeNZB™ is administered in a 0.5 ml by intramuscular injection to the anterolateral thigh or the deltoid region of the arm. Similar doses may be used for other delivery routes e.g. an intranasal OMV-based vaccine for atomisation may have a volume of about 100 µl or about 130 µl per spray, with four sprays administered to give a total dose of about 0.5 ml.

The pH of a composition of the invention is usually between 6 and 8, and more preferably between 6.5 and 7.5 (e.g. about 7). The pH of the RIVM OMV-based vaccine is 7.4 [74], and a pH <7.5 is preferred for compositions of the invention. The RIVM OMV-based vaccine maintains pH by using a 10 mM Tris/HCl buffer, and stable pH in compositions of the invention may be maintained by the use of a buffer e.g. a Tris buffer, a citrate buffer, phosphate buffer, or a histidine buffer. Thus compositions of the invention will generally include a buffer.

The composition may be sterile and/or pyrogen-free. Compositions of the invention may be isotonic with respect to humans.

Compositions of the invention for administration to patients are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the amount of protein per dose. A dose of about 0.9 mg protein per ml is typical for OMV-based intranasal vaccines.

Compositions of the invention may include an immunological adjuvant. Thus, for example, they may include an aluminium salt adjuvant or an oil-in-water emulsion (e.g. a squalene-in-water emulsion). Suitable aluminium salts include hydroxides (e.g. oxyhydroxides), phosphates (e.g. hydroxyphosphates, orthophosphates), (e.g. see chapters 8 & 9 of ref. 75), or mixtures thereof. The salts can take any suitable form (e.g. gel, crystalline, amorphous, etc.), with adsorption of antigen to the salt being preferred. The concentration of $Al^{+++}$ in a composition for administration to a patient is preferably less than 5 mg/ml e.g. ≤4 mg/ml, ≤3 mg/ml, ≤2 mg/ml, ≤1 mg/ml, etc. A preferred range is between 0.3 and 1 mg/ml. A maximum of 0.85 mg/dose is preferred. Aluminium hydroxide adjuvants are particularly suitable for use with meningococcal vaccines.

Meningococci affect various areas of the body and so the compositions of the invention may be prepared in various liquid forms. For example, the compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are typical.

Compositions of the invention may include an antimicrobial, particularly when packaged in multiple dose format. Antimicrobials such as thiomersal and 2-phenoxyethanol are commonly found in vaccines, but it is preferred to use either a mercury-free preservative or no preservative at all.

Compositions of the invention may comprise detergent e.g. a Tween (polysorbate), such as Tween 80. Detergents are generally present at low levels e.g. <0.01%.

Compositions of the invention may include residual detergent (e.g. deoxycholate) from OMV preparation. The amount of residual detergent is preferably less than 0.4 µg (more preferably less than 0.2 µg) for every jug of MenB protein.

If a composition of the invention includes LOS, the amount of LOS is preferably less than 0.12 µg (more preferably less than 0.05 µg) for every jug of protein.

Compositions of the invention may include sodium salts (e.g. sodium chloride) to give tonicity. A concentration of 10±2 mg/ml NaCl is typical e.g. about 9 mg/ml.

In addition to vesicles of the invention, immunogenic compositions can include soluble protein antigens. For instance, a useful composition can include vesicles of the invention in combination with one or more of (i) a NHBA antigen (ii) a NadA antigen and (iii) a fHbp antigen. For example, the vesicles can be mixed with the "4CMenB" vaccine (see above). In one useful embodiment, the composition includes fHbp both in soluble form and also in over-expressed vesicular form, with the two forms being different fHbp variants e.g. variant 1 in soluble form (as in 4CMenB) and variant 2 and/or 3 present in the surface of a vesicle, prepared from bacteria which express the variant 2 or 3 sequence from a promoter of the invention.

Thus one composition of the invention includes: (i) vesicles of the invention, such as spontaneously-released vesicles which display a fHbp sequence; (ii) a soluble NHBA antigen, such as SEQ ID NO: 4; (iii) a soluble fHbp antigen, such as SEQ ID NO: 5; and (iv) a soluble NadA antigen, such as SEQ ID NO: 6.

Methods of Treatment

The invention also provides a method for raising an immune response in a mammal, comprising administering a composition of the invention to the mammal. The immune response is preferably protective and preferably involves antibodies. The method may raise a booster response in a patient that has already been primed against *N. meningitidis*.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc.

The invention also provides vesicles of the invention for use as a medicament. The medicament is preferably used to raise an immune response in a mammal (i.e. it is an immunogenic composition) and is more preferably a vaccine.

The invention also provides the use of vesicles of the invention in the manufacture of a medicament for raising an immune response in a mammal.

These uses and methods are preferably for the prevention and/or treatment of a disease caused by *N.meningitidis* e.g. bacterial (or, more specifically, meningococcal) meningitis, or septicemia.

One way of checking efficacy of therapeutic treatment involves monitoring Neisserial infection after administration of the composition of the invention. One way of checking efficacy of prophylactic treatment involves monitoring immune responses against antigens after administration of the composition. Immunogenicity of compositions of the invention can be determined by administering them to test subjects (e.g. children 12-16 months age, or animal models [76]) and then determining standard parameters including serum bactericidal antibodies (SBA) and ELISA titres (GMT). These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

In general, compositions of the invention are able to induce serum bactericidal antibody responses after being administered to a subject. These responses are conveniently measured in mice and are a standard indicator of vaccine efficacy. Serum bactericidal activity (SBA) measures bacterial killing mediated by complement, and can be assayed using human or baby rabbit complement. WHO standards require a vaccine to induce at least a 4-fold rise in SBA in more than 90% of recipients. MeNZB™ elicits a 4-fold rise in SBA 4-6 weeks after administration of the third dose.

Preferred compositions can confer an antibody titre in a human subject patient that is superior to the criterion for seroprotection for an acceptable percentage of subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by any other suitable route. The invention may be used to elicit systemic and/or mucosal immunity. Intramuscular administration to the thigh or the upper arm is preferred. Injection may be via a needle (e.g. a hypodermic needle), but needle-free injection may alternatively be used. A typical intramuscular dose is 0.5 ml.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined. The OMV-based RIVM vaccine was tested using a 3- or 4-dose primary schedule, with vaccination at 0, 2 & 8 or 0, 1, 2 & 8 months. MeNZB™ is administered as three doses at six week intervals.

Compositions of the invention may be used to induce bactericidal antibody responses against more than one hypervirulent lineage of meningococcus. In particular, they can preferably induce bactericidal responses against two or three of the following three hypervirulent lineages: (i) cluster A4; (ii) ET5 complex; and (iii) lineage 3. They may additionally induce bactericidal antibody responses against one or more of hypervirulent lineages subgroup I, subgroup III, subgroup IV-1 or ET-37 complex, and against other lineages e.g. hyperinvasive lineages. This does not necessarily mean that the composition can induce bactericidal antibodies against each and every strain of meningococcus within these hypervirulent lineages e.g. rather, for any given group of four of more strains of meningococcus within a particular hypervirulent lineage, the antibodies induced by the composition are bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}$, $2^{11}$, $2^{12}$, $2^{13}$, $2^{14}$, $2^{15}$, $2^{16}$, $2^{17}$, $2^{18}$ or higher, preferably at least $2^{14}$) e.g. the serum is able to kill at least 50% of test bacteria of a particular strain when diluted 1/1024.

Useful compositions can induce bactericidal responses against the following strains of serogroup B meningococcus: (i) from cluster A4, strain 961-5945 (B:2b:P1.21,16) and/or strain G2136 (B:−); (ii) from ET-5 complex, strain MC58 (B:15:P1.7,16b) and/or strain 44/76 (B:15:P1.7,16); (iii) from lineage 3, strain 394/98 (B:4:P1.4) and/or strain BZ198 (B:NT:−). More preferred compositions can induce bactericidal responses against strains 961-5945, 44/76 and 394/98.

Strains 961-5945 and G2136 are both *Neisseria* MLST reference strains (ids 638 & 1002 in ref. 77). Strain MC58 is widely available (e.g. ATCC BAA-335) and was the strain sequenced in reference 78. Strain 44/76 has been widely used and characterised (e.g. ref. 79) and is one of the *Neisseria* MLST reference strains [id 237 in ref. 77; row 32 of Table 2 in ref. 46]. Strain 394/98 was originally isolated in New Zealand in 1998, and there have been several published studies using this strain (e.g. refs. 80 & 81). Strain BZ198 is another MLST reference strain (id 409 in ref. 77; row 41 of Table 2 in ref. 46).

Further Antigenic Components

In addition to vesicles of the invention, an immunogenic composition can include further non-vesicle antigens.

In some embodiments, a composition includes one or more capsular saccharides from meningococci e.g. from serogroups A, C, W135 and/or Y. These saccharides will usually be conjugated to a protein carrier. A composition of the invention may include one or more conjugates of capsular saccharides from 1, 2, 3, or 4 of meningococcal serogroups A, C, W135 and Y e.g. A+C, A+W135, A+Y, C+W135, C+Y, W135+Y, A+C+W135, A+C+Y, A+W135+Y, A+C+W135+Y, etc. Components including saccharides from all four of serogroups A, C, W135 and Y are ideal.

As well as containing antigens from *N.meningitidis*, compositions may include antigens from further pathogens. For example, the composition may comprise one or more of the following further antigens:

an antigen from *Streptococcus pneumoniae*, such as a saccharide (typically conjugated)

an antigen from hepatitis B virus, such as the surface antigen HBsAg.

an antigen from *Bordetella pertussis*, such as *pertussis* holotoxin (PT) and filamentous haemagglutinin (FHA)

from *B.pertussis*, optionally also in combination with pertactin and/or agglutinogens 2 and 3.

a diphtheria antigen, such as a diphtheria toxoid.

a tetanus antigen, such as a tetanus toxoid.

a saccharide antigen from *Haemophilus influenzae* B (Hib), typically conjugated.

inactivated poliovirus antigens.

Where a diphtheria antigen is included in the composition it is preferred also to include tetanus antigen and *pertussis* antigens. Similarly, where a tetanus antigen is included it is preferred also to include diphtheria and *pertussis* antigens. Similarly, where a *pertussis* antigen is included it is preferred also to include diphtheria and tetanus antigens. DTP combinations are thus preferred.

If a Hib saccharide is included (typically as a conjugate), the saccharide moiety may be a polysaccharide (e.g. full-length polyribosylribitol phosphate (PRP) as purified from bacteria), but it is also possible to fragment the purified saccharide to make oligosaccharides (e.g. MW from ~1 to ~5 kDa) e.g. by hydrolysis. The concentration of Hib conjugate in a composition will usually be in the range of 0.5 μg to 50 μg e.g. from 1-20 μg, from 10-15 μg, from 12-16 μg, etc. The amount may be about 15 g, or about 12.5 μg in some embodiments. A mass of less than 5 μg may be suitable [82] e.g. in the range 1-5 μg, 2-4 μg, or about 2.5 μg. As described above, in combinations that include Hib saccharide and meningococcal saccharides, the dose of the former may be selected based on the dose of the latter (in particular, with multiple meningococcal serogroups, their mean mass). Further characteristics of Hib conjugates are as disclosed above for meningococcal conjugates, including choice of carrier protein (e.g. CRM197 or tetanus toxoid), linkages, ratios, etc.

If a *S.pneumoniae* antigen is included, this may be a polypeptide or a saccharide. Conjugates capsular saccharides are particularly useful for immunising against pneumococcus. The saccharide may be a polysaccharide having the size that arises during purification of the saccharide from bacteria, or it may be an oligosaccharide achieved by fragmentation of such a polysaccharide. In the 7-valent PREVNAR™ product, for instance, 6 of the saccharides are presented as intact polysaccharides while one (the 18C serotype) is presented as an oligosaccharide. A composition may include a capsular saccharide from one or more of the following pneumococcal serotypes: 1, 2, 3, 4, 5, 6A, 6B, 7F, 8, 9N, 9V, 10A, 11A, 12F, 14, 15B, 17F, 18C, 19A, 19F, 20, 22F, 23F and/or 33F. A composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. Further characteristics of pneumococcal conjugates are as disclosed above for meningococcal conjugates, including choice of carrier protein (e.g. CRM197 or tetanus toxoid), linkages, ratios, etc. Where a composition includes more than one conjugate, each conjugate may use the same carrier protein or a different carrier protein. Reference 83 describes potential advantages when using different carrier proteins in multivalent pneumococcal conjugate vaccines.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 84-90, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

Where the invention concerns an "epitope", this epitope may be a B-cell epitope and/or a T-cell epitope, but will usually be a B-cell epitope. Such epitopes can be identified empirically (e.g. using PEPSCAN [91,92] or similar methods), or they can be predicted (e.g. using the Jameson-Wolf antigenic index [93], matrix-based approaches [94], MAP-ITOPE [95], TEPITOPE [96,97], neural networks [98], OptiMer & EpiMer [99, 100], ADEPT [101], Tsites [102], hydrophilicity [103], antigenic index [104] or the methods disclosed in references 105-109, etc.). Epitopes are the parts of an antigen that are recognised by and bind to the antigen binding sites of antibodies or T-cell receptors, and they may also be referred to as "antigenic determinants".

References to a percentage sequence identity between two amino acid sequences means that, when aligned, that percentage of amino acids are the same in comparing the two sequences. This alignment and % homology or sequence identity can be determined using software programs known in the art, for example those described in section 7.7.18 of ref. 110. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 111.

The word "substantially" does not exclude "completely" e.g. a composition which is "substantially free" from Y may be completely free from Y. Where necessary, the word "substantially" may be omitted from the definition of the invention.

BRIEF DESCRIPTION OF DRAWINGS

FIG. 2 illustrates comparative analysis of fHbp expression from porA and 16S modified promoters. The NZ98/254 strain expressing fHBP variant 2 under the control of the indicated promoters was grown on plates (A) and in liquid to logarithmic (B) and stationary phase (C) and levels of fHBP expression were measured by western blot from duplicate cultures (#1, #2) or from the benchmark overexpression strain. The unbroken arrow shows fHbp, whereas the lower broken arrow shows a loading control.

FIG. 3 shows expression of fHbp from three strains: (a) a ΔlpxL1 knockout; (b) a ΔsynX knockout; and (c) a ΔlpxL1ΔsynX double knockout. In all cases the knocked out gene(s) was replaced by fHbp under the control of a modified PorA promoter. Expression of fHbp was assessed by western blot on crude cell extracts using anti-fHbp serum, and was compared to Hfq as a control. FIG. 3A shows the western blot, and FIG. 3B quantifies expression in arbitrary units.

FIG. 4 shows fHbp levels in vesicles isolated from (i) ΔlpxL1ΔsynX and (ii) ΔlpxL1ΔsynXΔmltA knockout strains. FIG. 4A shows yield in mg/OD, and FIG. 4B is a western blot of 0.5 μg vesicles.

FIG. 5 shows expression of fHbp in two strains that overexpress either variant 1 or variant 2 fHbp in distinct loci (lanes c & d) or a strain that overexpresses both variant 1 and variant 2 in respective loci (lane e). Lane a is the wild-type strain, and lane b is a ΔfHbp knockout of that strain.

FIG. 6 shows silver-stained SDS-PAGE of vesicles purified from the triple knockout.

MODES FOR CARRYING OUT THE INVENTION

Modified PorA Promoters

The sequences upstream of the transcription start site of two phase variants of the wild-type meningococcal porA promoter, containing 11 and 13 consecutive Gs in the spacer region, are as follows, with the −35 and −10 regions underlined:

```
                                    (SEQ ID NO: 31)
AAAAATGGTTTTTTGCGGGGGGGGGGGTATAATTGAAGAC (SEQ ID NO: 40)
AAAAATGGTTTTTTGCGGGGGGGGGGGGGTATAATTGAAGAC
```

The intervening sequence between the −35 and −10 regions includes a $G_{11}$ poly-G sequence which is connected to phase variation of PorA expression. To stabilise expression from this promoter, three modifications were tested (modifications in lower case):

```
                               ("ST1"; SEQ ID NO: 32)
AAAAATGGTTTTTTGCGaGGGaGGtGGTATAATTGAAGAC ("ST2"; SEQ ID NO: 33)
AAAAATtGacaTTTGCGaGGGaGGtGGTATAATTGAAGAC
```

-continued

```
                               ("ST3"; SEQ ID NO: 34)
AAAAtTGacaTTTTGCGaGGGaGGtGGTATAATTGAAGAC
```

Thus in "ST1" the $G_{11}$ sequence was interrupted in three places, leaving no more than 3 consecutive G residues. In "ST2" the same intervening sequence was used, but the −35 region was substituted by a consensus −35 region TTGACA. In "ST3" an extra T residue was inserted immediately downstream of the −35 region.

These three promoters were used to drive expression of a fHbp sequence (fHbp variant 2) in the NZ98/258 strain. All three modified promoters resulted in high level overexpression of fHBP in the strain when compared to an equivalent overexpressing strain which has been reported in the literature [112,113]. The best expression was seen with ST2 (FIGS. 1 & 2).

Modified rRNA Promoters

In further experiments the 16S rRNA promoter was fused to the 5' UTR of the porA gene:

```
                                    (SEQ ID NO: 35)
ATATCTTGACAGGCGGAAGGAATACTTTATAATTCGCAAC . . .
```

This promoter was subjected to mutation and three variants downstream of the −35 region were sequenced as follows:

```
                               ("wt"; SEQ ID NO: 35)
ATATCTTGACAGGCGGAAGGAATACTTTATAATTCGCAAC ("#5"; SEQ ID NO: 36)
ATATCTTGACAGGCGGAAGGAATACTTTATATTCGCAAC . . .

("#6"; SEQ ID NO: 37)
ATATCTTGACAGGCGGAAGGAATACTTTTAATTCGCAC . . .

("#8"; SEQ ID NO: 38)
ATATCTTGACAGGCGGAAGGAAACTTTATAATTCGCAAC . . .
```

Thus in variants #5 and #6 the −10 sequence is a 5-mer, and variant #6 also lost a nucleotide between the −10 region and the transcription start site. In variant #8 the −10 region and its downstream sequence are the same as wt, but the intervening sequence between the −35 and −10 regions is one nucleotide shorter than wt.

Expression of fHbp from Modified Promoters

These promoters were fused to the 5'UTR region of the porA gene and used to drive expression of the fHbp coding sequence. As seen in FIG. 2, variants #5 and #6, variants #5 and #6 showed the strongest expression, approaching levels seen with ST2.

The complete region spanning the wild-type promoter (SEQ ID NO: 35), extending downstream into the transcribed region and also upstream, was as follows (SEQ ID NO: 41; 358mer), with the −35 and −10 regions underlined, and nucleotide +1 (following reference 10) double-underlined:

```
                                                                      (SEQ ID NO: 41)
. . . CGTCTGAGTCCCCGAGTTTCAGACAGCATATTCACAAAGGCGCACCAGCCGGAGGAGGGAGAGGAAAG

GATTGTTGGAGGCGGCGCAGTATTTAGCAGAAATAAAAAACCTTATCCGACAGCGACATGACGAATTTCCC

CAAAAAAATCCCGCTGAAAGCATTGACCGTTTTTCCCTGTGGGCGTATAGTTCGGTTCTTCGCTGCTGCAG

AAGTGGCGGACGAACTGAAAAGTATAGCACAGAATGTTGGGGATATCGAGAGATATCTTGACAGGCGGAAG

GAATACTTTATAATTCGCAACGTATCGGGTGTTTGCCCGATGTTTTTAGGTTTTTATCAAATTTACAAAAG

GAAGCC . . .
```

Similarly, the surrounding sequences for variants #5 and #6 were as follows:

(SEQ ID NO: 42)
5: . . . CGTCTGAGTCCCCGAGTTTCAGACAGCATATTCACAAAGGCGCACCAGCCGGAGGAGGGAGAGG

AAAGGATTGTTGGAGGCGGCGCAGTATTTAGCAGAAATAAAAAACCTTATCCGACAGCGACATGACGAATT

TCCCCAAAAAAATCCCGCTGAAAGCATTGACCGTTTTTCCCTGTGGGCGTATAGTTCGGTTCTTCGCTGCT

GCAGAAGTGGCGGACGAACTGAAAAGTATAGCACAGAATGTTGGGGATATCGAGAGATATC<u>TTGAC</u>AGGCG

GAAGGAATACTT<u>TATAT</u>TCGCAAC<u>G</u>TATCGGGTGTTTGCCNNANGTTTTTAGGTTTTTATCAAATTTCAAA

AGGAAGCC . . .

(SEQ ID NO: 43)
6: . . . CGTCTGAGTCCCCGAGTTTCAGACAGCATATTCACAAAGGCGCACCAGCCGGAGGAGGGAGAGG

AAAGGATTGTTGGAGGCGGCGCAGTATTTAGCAGAAATAAAAAACCTTATCCGACAGCGACATGACGAATT

TCCCCAAAAAAATCCCGCTGAAAGCATTGACCGTTTTTCCCTGTGGGCGTATAGTTCGGTTCTTCGCTGCT

GCAGAAGTGGCGGACGAACTGAAAAGTATAGCACAGAATGTTGGGGATATCGAGAGATATC<u>TTGAC</u>AGGCG

GAAGGAATACTTT<u>TTAAT</u>TCGCAC<u>G</u>TATCGGGTGTTTGCCCGATGTTTTTAGGTTTTTATTAAATTTACAAA

AGGAAGCCCATANGAATCGAACTGC . . .

Any of these longer sequences can be used with the invention, although modifications as discussed herein may, of course, be made.

A fHbp gene under the control of a variant promoter was stably inserted into the chromosome of a meningococcus (strain NZ98/254) in place of the endogenous lpxL1 and/or synX gene(s). Slightly higher expression levels were seen at the synX locus, and expression for the strain with both insertions (ΔlpxL1ΔsynX double knockout) was the sum of the expression from the individual loci (FIG. 3).

Figure 1:
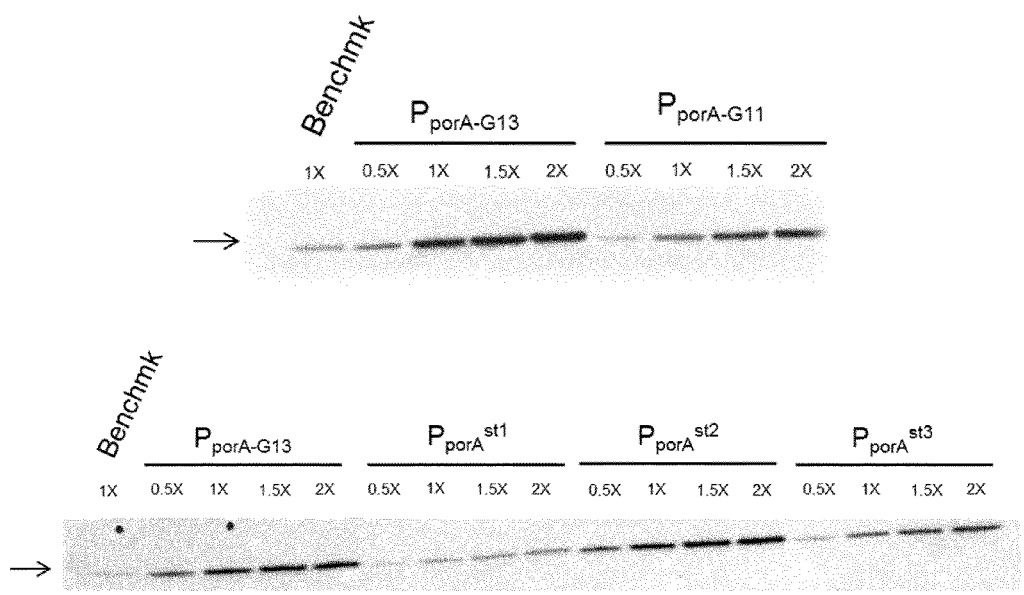
FIG. 1 illustrates fHbp expression levels in the same background strain (NZ98/254) using five different promoters and the benchmark strain overexpressing the same fHbp allele in the same background [112,113]. A variant 2 allele of fHbp was overexpressed in the benchmark strain or from either 2 wildtype phase variants of the porA promoter with either 11 Gs or 13 Gs in the spacer tract or with the modified ST1, ST2 and ST3 porA promoters as indicated. Western blotting of equivalent quantities of total protein were loaded from 0.5× to 2× as indicated for each strain, and the arrow shows fHbp.
Figure 5:
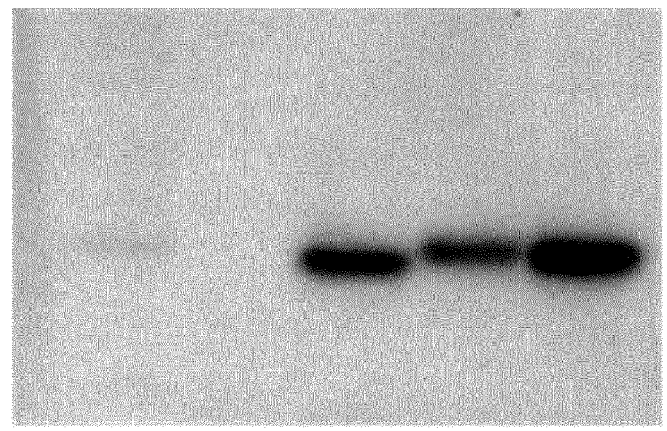
Figure 6:
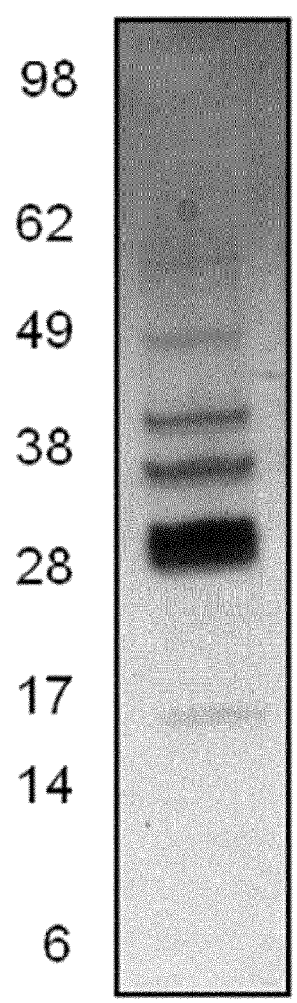

Strains were also made in which two different fHbp variants (1 & 2) were expressed under the control of a modified PorA promoter. The co-expression of both variants has no significant negative effect on the expression from each distinct locus, and instead resulted in an additive effect (FIG. 5).

Knockout of the endogenous mltA (GNA33) gene in the ΔlpxL1ΔsynX double knockout further increased expression levels, and had no negative impact on the localisation of fHbp protein to the strain's vesicles. FIG. 4 shows fHbp levels in vesicles isolated from these strains, showing (A) the yield of protein (mg) relative to the culture's optical density (OD), and (B) an anti-fHbp western blot against of 0.5 μg of the vesicles. SDS-PAGE shows that the fHbp band in the triple knockout strain was one of the most abundant proteins in the vesicles, along with PorA and PorB (FIG. 6).

It will be understood that the invention is described above by way of example only and modifications may be made whilst remaining within the scope and spirit of the invention.

REFERENCES

[1] Koeberling et al. (2007) *Vaccine* 25:1912-20.
[2] Koeberling et al. (2008) *J Infect Dis* 198:262-70.
[3] Hou et al. (2005) *J Infect Dis* 192:580-90.
[4] WO2009/038889.
[5] Bonvehi et al. (2010) *Clin Vacc Immunol* 17:1460-6.
[6] Keiser et al. (2011) *Vaccine* 29:1413-20.
[7] Pinto et al. (2011) *Vaccine* 29:7752-8.
[8] WO01/09350.
[9] WO2004/015099.
[10] van der Ende et al. (1995) *J Bacteriol* 177:2475-80.
[11] Gourse et al. (1986) *Cell* 44:197-205.
[12] Hirvonene et al. (2001) *J. Bacteriol.* 183:6305-14.
[13] Deghmane et al. (2003) *Infect Immun* 71:2897-901.
[14] WO02/09643.
[15] Katial et al. (2002) *Infect. Immun.* 70:702-707.
[16] U.S. Pat. No. 6,180,111.
[17] WO01/34642.
[18] WO2006/046143.
[19] WO2004/019977.
[20] European patent 0011243.
[21] Fredriksen et al. (1991) *NIPH Ann.* 14 (2):67-80.
[22] WO01/91788.
[23] WO2005/004908.
[24] WO2011/036562.
[25] WO00/26384.
[26] U.S. Pat. No. 6,531,131
[27] U.S. Pat. No. 6,645,503
[28] Claassene et al. (1996) *Vaccine* 14:1001-8.
[29] de Kleijne et al. (2000) *Vaccine* 18:1456-66.
[30] WO03/105890.
[31] WO2006/024946
[32] WO2006/081259.
[33] Schielke et al. (2009) *Mol Microbiol* 72:1054-67.
[34] WO2004/014418.
[35] WO00/25811.
[36] WO2010/070453.
[37] WO02/09746.
[38] Oriente et al. (2010) *J Bacteriol* 192:691-701.
[39] U.S. provisional patent application 61/247,428.
[40] Giuliani et al. (2006) *Proc Natl Acad Sci USA* 103 (29): 10834-9.
[41] Donnelly et al. (2010) *PNAS USA* 107:19490-5.
[42] Kimura et al. (2010) *Clin Vaccine Immunol.* 2010 PMID: 21177912.
[43] Zollinger et al. (2010) *Vaccine* 28:5057-67.
[44] WO99/10497.
[45] Steeghs et al. (2001) *The EMBO Journal* 20:6937-6945.
[46] Maiden et al. (1998) *PNAS USA* 95:3140-3145.
[47] WO02/062378.
[48] WO2004/014417.
[49] WO00/66741.
[50] WO99/57280
[51] Serruto et al. (2010) *PNAS USA* 107:3770-5.

[52] U.S. Pat. No. 5,698,438.
[53] Perkins-Balding et al. (2003) *Microbiology* 149:3423-35.
[54] Masignani et al. (2003) *J Exp Med* 197:789-799.
[55] Welsch et al. (2004) *J Immunol* 172:5605-15.
[56] Hou et al. (2005) *J Infect Dis* 192(4):580-90.
[57] WO03/063766.
[58] Fletcher et al. (2004) *Infect Immun* 72:2088-2100.
[59] Zhu et al. (2005) *Infect Immun* 73(10):6838-45.
[60] Cantini et al. (2006) *J. Biol. Chem.* 281:7220-7227
[61] WO2004/048404
[62] WO2009/104097.
[63] Schneider et al. (2009) *Nature* 458:890-3.
[64] WO2010/046715.
[65] Pajon et al. (2012) *Infect Immun* 80:2667-77.
[66] WO2011/126863.
[67] Martin et al. (1997) *J Exp Med* 185(7): 1173-83.
[68] WO96/29412.
[69] WO01/55182.
[70] WO01/38350.
[71] WO00/23595.
[72] Gennaro (2000) *Remington: The Science and Practice of Pharmacy.* 20th edition, ISBN: 0683306472.
[73] RIVM report 124001 004.
[74] RIVM report 000012 003.
[75] *Vaccine Design* . . . (1995) eds. Powell & Newman. ISBN: 030644867X. Plenum.
[76] WO01/30390.
[77] http://neisseria.org/nm/typing/mlst/
[78] Tettelin et al. (2000) *Science* 287:1809-1815.
[79] Pettersson et al. (1994) *Microb Pathog* 17 (6):395-408.
[80] Welsch et al. (2002) Thirteenth International Pathogenic Neisseria Conference, Norwegian Institute of Public Health, Oslo, Norway; Sep. 1-6, 2002. *Genome-derived antigen (GNA) 2132 elicits protective serum antibodies to groups B and C Neisseria meningitidis strains.*
[81] Santos et al. (2002) Thirteenth International Pathogenic Neisseria Conference, Norwegian Institute of Public Health, Oslo, Norway; Sep. 1-6, 2002. *Serum bactericidal responses in rhesus macaques immunized with novel vaccines containing recombinant proteins derived from the genome of N. meningitidis.*
[82] WO2007/000327.
[83] WO2007/071707
[84] *Methods In Enzymology* (S. Colowick and N. Kaplan, eds., Academic Press, Inc.)
[85] *Handbook of Experimental Immunology*, Vols. I-IV (D. M. Weir and C. C. Blackwell, eds, 1986, Blackwell Scientific Publications)
[86] Sambrook et al. (2001) *Molecular Cloning: A Laboratory Manual,* 3rd edition (Cold Spring Harbor Laboratory Press).
[87] *Handbook of Surface and Colloidal Chemistry* (Birdi, K. S. ed., CRC Press, 1997)
[88] Ausubel et al. (eds) (2002) *Short protocols in molecular biology,* 5th edition (Current Protocols).
[89] *Molecular Biology Techniques: An Intensive Laboratory Course,* (Ream et al, eds., 1998, Academic Press)
[90] *PCR (Introduction to Biotechniques Series),* 2nd ed. (Newton & Graham eds., 1997, Springer Verlag)
[91] Geysen et al. (1984) *PNAS USA* 81:3998-4002.
[92] Carter (1994) *Methods Mol Biol* 36:207-23.
[93] Jameson, B A et al. 1988, *CABIOS* 4 (1): 181-186.
[94] Raddrizzani & Hammer (2000) *Brief Bioinform* 1 (2): 179-89.
[95] Bublil et al. (2007) *Proteins* 68 (1):294-304.
[96] De Lalla et al. (1999) *J. Immunol.* 163:1725-29.
[97] Kwok et al. (2001) *Trends Immunol* 22:583-88.
[98] Brusic et al. (1998) *Bioinformatics* 14 (2):121-30
[99] Meister et al. (1995) *Vaccine* 13 (6):581-91.
[100] Roberts et al. (1996) *AIDS Res Hum Retroviruses* 12 (7):593-610.
[101] Maksyutov & Zagrebelnaya (1993) *Comput Appl Biosci* 9 (3):291-7.
[102] Feller & de la Cruz (1991) *Nature* 349 (6311):720-1.
[103] Hopp (1993) *Peptide Research* 6:183-190.
[104] Welling et al. (1985) *FEBS Lett.* 188:215-218.
[105] Davenport et al. (1995) *Immunogenetics* 42:392-297.
[106] Tsurui & Takahashi (2007) *J Pharmacol Sci.* 105 (4):299-316.
[107] Tong et al. (2007) *Brief Bioinform.* 8 (2):96-108.
[108] Schirle et al. (2001) *J Immunol Methods.* 257 (1-2): 1-16.
[109] Chen et al. (2007) *Amino Acids* 33 (3):423-8.
[110] *Current Protocols in Molecular Biology* (F. M. Ausubel et al., eds., 1987) Supplement 30
[111] Smith & Waterman (1981) *Adv. Appl. Math.* 2: 482-489.
[112] Koeberling et al. (2009) *Clin Vaccin Immunol* 16:156-62.
[113] Koeberling et al. (2011) *Vaccine* 29:4728-34.

The invention claimed is:

1. A nucleic acid comprising a promoter operably linked to a heterologous coding sequence, wherein the promoter is selected from the group consisting of:
(a) a promoter comprising
  (i) a −10 region from a meningococcal porA gene promoter comprising TATAAT and
  (ii) a −35 region comprising the nucleic acid sequence TGGTTT or the nucleic acid sequence TTGACA,
wherein the −10 region and the −35 region are separated by an intervening sequence comprising 12-20 nucleotides, wherein the intervening sequence either comprises no poly-G sequence or includes a poly-G sequence comprising no more than five consecutive G nucleotides; and
(b) a promoter comprising a sequence selected from the group consisting of
  (i) the sequence of SEQ ID NO: 18 and
  (ii) a variant of SEQ ID NO: 18 which differs from SEQ ID NO: 18 by up to 4 single-nucleotide insertions, deletions, or substitutions.

2. The nucleic acid of claim 1, wherein the promoter of (a) has a nucleic acid sequence selected from the group consisting of: SEQ ID NO: 32, SEQ ID NO: 33, and SEQ ID NO: 34.

3. The nucleic acid of claim 1, wherein the intervening sequence does not comprise a sequence GGGGG.

4. The nucleic acid of claim 1, wherein non-transcribed sequence downstream of the −10 sequence and upstream of the transcription start site comprises 5-10 nucleotides.

5. The nucleic acid of claim 1, wherein the promoter of (a) comprises the sequence of SEQ ID NO: 30.

6. The nucleic acid of claim 1, wherein the promoter of (b) is selected from the group consisting of: nucleotides 6-39 of SEQ ID NO: 36, nucleotides 6-38 of SEQ ID NO: 37, and nucleotides 6-39 of SEQ ID NO: 38.

7. A bacterial expression vector comprising a DNA sequence comprising the nucleic acid of claim 1.

8. A meningococcus comprising a DNA sequence comprising the nucleic acid of claim 1.

9. The meningococcus of claim 8, wherein the heterologous coding sequence encodes an outer membrane protein.

10. The meningococcus of claim 9, wherein the outer membrane protein is a fHbp.

11. The meningococcus of claim 8, wherein the meningococcus does not express an active MltA.

12. The meningococcus of claim 8, wherein the meningococcus comprises a knockout of at least one of SynX and LpxL1.

13. The meningococcus of claim 8 comprising a meningococcus selected from the group consisting of serogroup B and serogroup W135.

14. The meningococcus of claim 8 comprising a lipopolysaccharide of immunotype L3.

15. The nucleic acid of claim 4, wherein the non-transcribed sequence comprises a sequence selected from the group consisting of TGAAGAC and TCGCAAC.

* * * * *

SEQUENCE LISTING

```
<160> NUMBER OF SEQ ID NOS: 43

<210> SEQ ID NO 1
<211> LENGTH: 248
<212> TYPE: PRT
<213> ORGANISM: Neisseria meningitidis

<400> SEQUENCE: 1

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60
```

-continued

```
Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
             85                  90                  95

Ser Ala Leu Thr Ala Phe Gln Thr Gln Ile Gln Asp Ser Glu His
         100                 105                 110

Ser Gly Lys Met Val Ala Lys Arg Gln Phe Arg Ile Gly Asp Ile Ala
         115                 120                 125

Gly Glu His Thr Ser Phe Asp Lys Leu Pro Glu Gly Gly Arg Ala Thr
     130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                 165                 170                 175

Leu Lys Ser Pro Glu Leu Asn Val Asp Leu Ala Ala Ala Asp Ile Lys
             180                 185                 190

Pro Asp Gly Lys Arg His Ala Val Ile Ser Gly Ser Val Leu Tyr Asn
         195                 200                 205

Gln Ala Glu Lys Gly Ser Tyr Ser Leu Gly Ile Phe Gly Gly Lys Ala
     210                 215                 220

Gln Glu Val Ala Gly Ser Ala Glu Val Lys Thr Val Asn Gly Ile Arg
225                 230                 235                 240

His Ile Gly Leu Ala Ala Lys Gln
                 245

<210> SEQ ID NO 2
<211> LENGTH: 247
<212> TYPE: PRT
<213> ORGANISM: Neisseria meningitidis

<400> SEQUENCE: 2

Val Ala Ala Asp Ile Gly Ala Gly Leu Ala Asp Ala Leu Thr Ala Pro
  1               5                  10                  15

Leu Asp His Lys Asp Lys Ser Leu Gln Ser Leu Thr Leu Asp Gln Ser
             20                  25                  30

Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
     50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Ile Tyr Lys Gln Asp His
             85                  90                  95

Ser Ala Val Val Ala Leu Gln Ile Glu Lys Ile Asn Asn Pro Asp Lys
         100                 105                 110

Ile Asp Ser Leu Ile Asn Gln Arg Ser Phe Leu Val Ser Gly Leu Gly
     115                 120                 125

Gly Glu His Thr Ala Phe Asn Gln Leu Pro Asp Gly Lys Ala Glu Tyr
     130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                 165                 170                 175

Lys Thr Pro Glu Gln Asn Val Glu Leu Ala Ala Ala Glu Leu Lys Ala
```

```
                180                 185                 190
Asp Glu Lys Ser His Ala Val Ile Leu Gly Asp Thr Arg Tyr Gly Ser
            195                 200                 205

Glu Glu Lys Gly Thr Tyr His Leu Ala Leu Phe Gly Asp Arg Ala Gln
        210                 215                 220

Glu Ile Ala Gly Ser Ala Thr Val Lys Ile Gly Lys Val His Glu
225                 230                 235                 240

Ile Gly Ile Ala Gly Lys Gln
                245

<210> SEQ ID NO 3
<211> LENGTH: 250
<212> TYPE: PRT
<213> ORGANISM: Neisseria meningitidis

<400> SEQUENCE: 3

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 4
<211> LENGTH: 644
<212> TYPE: PRT
<213> ORGANISM: Artificial Sequence
<220> FEATURE:
<223> OTHER INFORMATION: Hybrid meningococcal antigen

<400> SEQUENCE: 4
```

```
Met Ala Ser Pro Asp Val Lys Ser Ala Asp Thr Leu Ser Lys Pro Ala
1               5                   10                  15
Ala Pro Val Val Ser Glu Lys Glu Thr Glu Ala Lys Glu Asp Ala Pro
                20                  25                  30
Gln Ala Gly Ser Gln Gly Gln Gly Ala Pro Ser Ala Gln Gly Gly Gln
            35                  40                  45
Asp Met Ala Ala Val Ser Glu Glu Asn Thr Gly Asn Gly Gly Ala Ala
    50                  55                  60
Ala Thr Asp Lys Pro Lys Asn Glu Asp Glu Gly Ala Gln Asn Asp Met
65              70                  75                  80
Pro Gln Asn Ala Ala Asp Thr Asp Ser Leu Thr Pro Asn His Thr Pro
                85                  90                  95
Ala Ser Asn Met Pro Ala Gly Asn Met Glu Asn Gln Ala Pro Asp Ala
                100                 105                 110
Gly Glu Ser Glu Gln Pro Ala Asn Gln Pro Asp Met Ala Asn Thr Ala
                115                 120                 125
Asp Gly Met Gln Gly Asp Asp Pro Ser Ala Gly Gly Glu Asn Ala Gly
    130                 135                 140
Asn Thr Ala Ala Gln Gly Thr Asn Gln Ala Glu Asn Asn Gln Thr Ala
145                 150                 155                 160
Gly Ser Gln Asn Pro Ala Ser Ser Thr Asn Pro Ser Ala Thr Asn Ser
                165                 170                 175
Gly Gly Asp Phe Gly Arg Thr Asn Val Gly Asn Ser Val Val Ile Asp
                180                 185                 190
Gly Pro Ser Gln Asn Ile Thr Leu Thr His Cys Lys Gly Asp Ser Cys
                195                 200                 205
Ser Gly Asn Asn Phe Leu Asp Glu Glu Val Gln Leu Lys Ser Glu Phe
                210                 215                 220
Glu Lys Leu Ser Asp Ala Asp Lys Ile Ser Asn Tyr Lys Lys Asp Gly
225                 230                 235                 240
Lys Asn Asp Gly Lys Asn Asp Lys Phe Val Gly Leu Val Ala Asp Ser
                245                 250                 255
Val Gln Met Lys Gly Ile Asn Gln Tyr Ile Ile Phe Tyr Lys Pro Lys
                260                 265                 270
Pro Thr Ser Phe Ala Arg Phe Arg Arg Ser Ala Arg Ser Arg Arg Ser
                275                 280                 285
Leu Pro Ala Glu Met Pro Leu Ile Pro Val Asn Gln Ala Asp Thr Leu
                290                 295                 300
Ile Val Asp Gly Glu Ala Val Ser Leu Thr Gly His Ser Gly Asn Ile
305                 310                 315                 320
Phe Ala Pro Glu Gly Asn Tyr Arg Tyr Leu Thr Tyr Gly Ala Glu Lys
                325                 330                 335
Leu Pro Gly Gly Ser Tyr Ala Leu Arg Val Gln Gly Glu Pro Ser Lys
                340                 345                 350
Gly Glu Met Leu Ala Gly Thr Ala Val Tyr Asn Gly Glu Val Leu His
                355                 360                 365
Phe His Thr Glu Asn Gly Arg Pro Ser Pro Ser Arg Gly Arg Phe Ala
                370                 375                 380
Ala Lys Val Asp Phe Gly Ser Lys Ser Val Asp Gly Ile Ile Asp Ser
385                 390                 395                 400
Gly Asp Gly Leu His Met Gly Thr Gln Lys Phe Lys Ala Ala Ile Asp
                405                 410                 415
```

Gly Asn Gly Phe Lys Gly Thr Trp Thr Glu Asn Gly Gly Asp Val
                420                 425                 430

Ser Gly Lys Phe Tyr Gly Pro Ala Gly Glu Val Ala Gly Lys Tyr
            435                 440                 445

Ser Tyr Arg Pro Thr Asp Ala Glu Lys Gly Gly Phe Gly Val Phe Ala
450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
        595                 600                 605

Asp Phe Ser Thr Thr Ile Asp Arg Thr Lys Trp Gly Val Asp Tyr Leu
610                 615                 620

Val Asn Val Gly Met Thr Lys Ser Val Arg Ile Asp Ile Gln Ile Glu
625                 630                 635                 640

Ala Ala Lys Gln

<210> SEQ ID NO 5
<211> LENGTH: 434
<212> TYPE: PRT
<213> ORGANISM: Artificial Sequence
<220> FEATURE:
<223> OTHER INFORMATION: Hybrid meningococcal antigen

<400> SEQUENCE: 5

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asp Arg His
50                  55                  60

Leu Leu Leu Leu Gly Gln Val Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Arg Ala Arg Val Lys Ile Val Thr Tyr Gly Asn Val Thr Tyr

```
                130                 135                 140
Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
            210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
                260                 265                 270

Gly Glu Phe Gln Val Tyr Lys Gln Ser His Ser Ala Leu Thr Ala Phe
            275                 280                 285

Gln Thr Glu Gln Ile Gln Asp Ser Glu His Ser Gly Lys Met Val Ala
            290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
            355                 360                 365

Asn Val Asp Leu Ala Ala Ala Asp Ile Lys Pro Asp Gly Lys Arg His
            370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln

<210> SEQ ID NO 6
<211> LENGTH: 327
<212> TYPE: PRT
<213> ORGANISM: Neisseria meningitidis

<400> SEQUENCE: 6

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
                20                  25                  30

Thr Ile Tyr Asp Ile Asp Glu Asp Gly Thr Ile Thr Lys Lys Asp Ala
                35                  40                  45

Thr Ala Ala Asp Val Glu Ala Asp Asp Phe Lys Gly Leu Gly Leu Lys
            50                  55                  60

Lys Val Val Thr Asn Leu Thr Lys Thr Val Asn Glu Asn Lys Gln Asn
```

```
                65                  70                  75                  80
Val Asp Ala Lys Val Lys Ala Ala Glu Ser Glu Ile Glu Lys Leu Thr
                    85                  90                  95

Thr Lys Leu Ala Asp Thr Asp Ala Ala Leu Ala Asp Thr Asp Ala Ala
                100                 105                 110

Leu Asp Ala Thr Thr Asn Ala Leu Asn Lys Leu Gly Glu Asn Ile Thr
                115                 120                 125

Thr Phe Ala Glu Glu Thr Lys Thr Asn Ile Val Lys Ile Asp Glu Lys
            130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
                180                 185                 190

Asn Val Asp Ala Lys Val Lys Ala Ala Glu Thr Ala Ala Gly Lys Ala
            195                 200                 205

Glu Ala Ala Ala Gly Thr Ala Asn Thr Ala Ala Asp Lys Ala Glu Ala
            210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
            275                 280                 285

His Asp Thr Arg Leu Asn Gly Leu Asp Lys Thr Val Ser Asp Leu Arg
            290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325

<210> SEQ ID NO 7
<211> LENGTH: 792
<212> TYPE: PRT
<213> ORGANISM: Neisseria meningitidis

<400> SEQUENCE: 7

Met Lys Pro Leu Gln Met Leu Pro Ile Ala Ala Leu Val Gly Ser Ile
1               5                   10                  15

Phe Gly Asn Pro Val Leu Ala Ala Asp Glu Ala Thr Glu Thr Thr
                20                  25                  30

Pro Val Lys Ala Glu Ile Lys Ala Val Arg Val Lys Gly Gln Arg Asn
            35                  40                  45

Ala Pro Ala Ala Val Glu Arg Val Asn Leu Asn Arg Ile Lys Gln Glu
        50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110
```

```
Ser Glu Glu Asn Ser Leu Tyr Ala Arg Tyr Gly Asn Phe Asn Ser Ser
        115                 120                 125
Arg Leu Ser Ile Asp Pro Glu Leu Val Arg Asn Ile Glu Ile Val Lys
130                 135                 140
Gly Ala Asp Ser Phe Asn Thr Gly Ser Gly Ala Leu Gly Gly Gly Val
145                 150                 155                 160
Asn Tyr Gln Thr Leu Gln Gly Arg Asp Leu Leu Asp Asp Arg Gln
            165                 170                 175
Phe Gly Val Met Met Lys Asn Gly Tyr Ser Thr Arg Asn Arg Glu Trp
                180                 185                 190
Thr Asn Thr Leu Gly Phe Gly Val Ser Asn Asp Arg Val Asp Ala Ala
            195                 200                 205
Leu Leu Tyr Ser Gln Arg Arg Gly His Glu Thr Glu Ser Ala Gly Asn
210                 215                 220
Arg Gly Tyr Ala Val Glu Gly Glu Gly Ser Gly Ala Asn Ile Arg Gly
225                 230                 235                 240
Ser Ala Arg Gly Ile Pro Asp Ser Ser Lys His Lys Tyr Asn His His
                245                 250                 255
Ala Leu Gly Lys Ile Ala Tyr Gln Ile Asn Asp Asn His Arg Ile Gly
            260                 265                 270
Ala Ser Leu Asn Gly Gln Gln Gly His Asn Tyr Thr Val Glu Glu Ser
        275                 280                 285
Tyr Asn Leu Thr Ala Ser Ser Trp Arg Glu Ala Asp Asp Val Asn Arg
    290                 295                 300
Arg Arg Asn Ala Asn Leu Phe Tyr Glu Trp Met Pro Asp Ser Asn Trp
305                 310                 315                 320
Leu Ser Ser Leu Lys Ala Asp Phe Asp Tyr Gln Lys Thr Lys Val Ala
                325                 330                 335
Ala Val Asn Asn Lys Gly Ser Phe Pro Met Asp Tyr Ser Thr Trp Thr
            340                 345                 350
Arg Asn Tyr Asn Gln Lys Asp Leu Asp Glu Ile Tyr Asn Arg Ser Met
        355                 360                 365
Asp Thr Arg Phe Lys Arg Phe Thr Leu Arg Leu Asp Ser His Pro Leu
    370                 375                 380
Gln Leu Gly Gly Gly Arg His Arg Leu Ser Phe Lys Thr Phe Val Ser
385                 390                 395                 400
Arg Arg Asp Phe Glu Asn Leu Asn Arg Asp Asp Tyr Tyr Phe Ser Gly
                405                 410                 415
Arg Val Val Arg Thr Thr Ser Ser Ile Gln His Pro Val Lys Thr Thr
            420                 425                 430
Asn Tyr Gly Phe Ser Leu Ser Asp Gln Ile Gln Trp Asn Asp Val Phe
        435                 440                 445
Ser Ser Arg Ala Gly Ile Arg Tyr Asp His Thr Lys Met Thr Pro Gln
    450                 455                 460
Glu Leu Asn Ala Glu Cys His Ala Cys Asp Lys Thr Pro Pro Ala Ala
465                 470                 475                 480
Asn Thr Tyr Lys Gly Trp Ser Gly Phe Val Gly Leu Ala Ala Gln Leu
                485                 490                 495
Asn Gln Ala Trp Arg Val Gly Tyr Asp Ile Thr Ser Gly Tyr Arg Val
            500                 505                 510
Pro Asn Ala Ser Glu Val Tyr Phe Thr Tyr Asn His Gly Ser Gly Asn
        515                 520                 525
Trp Leu Pro Asn Pro Asn Leu Lys Ala Glu Arg Ser Thr Thr His Thr
```

```
                530                 535                 540
Leu Ser Leu Gln Gly Arg Ser Glu Lys Gly Met Leu Asp Ala Asn Leu
545                 550                 555                 560

Tyr Gln Ser Asn Tyr Arg Asn Phe Leu Ser Glu Glu Gln Lys Leu Thr
                565                 570                 575

Thr Ser Gly Thr Pro Gly Cys Thr Glu Glu Asn Ala Tyr Tyr Gly Ile
                580                 585                 590

Cys Ser Asp Pro Tyr Lys Glu Lys Leu Asp Trp Gln Met Lys Asn Ile
                595                 600                 605

Asp Lys Ala Arg Ile Arg Gly Ile Glu Leu Thr Gly Arg Leu Asn Val
                610                 615                 620

Asp Lys Val Ala Ser Phe Val Pro Glu Gly Trp Lys Leu Phe Gly Ser
625                 630                 635                 640

Leu Gly Tyr Ala Lys Ser Lys Leu Ser Gly Asp Asn Ser Leu Leu Ser
                645                 650                 655

Thr Gln Pro Leu Lys Val Ile Ala Gly Ile Asp Tyr Glu Ser Pro Ser
                660                 665                 670

Glu Lys Trp Gly Val Phe Ser Arg Leu Thr Tyr Leu Gly Ala Lys Lys
                675                 680                 685

Val Lys Asp Ala Gln Tyr Thr Val Tyr Glu Asn Lys Gly Trp Gly Thr
                690                 695                 700

Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Ala Lys Asn Leu Thr
                725                 730                 735

Leu Arg Ala Gly Val Tyr Asn Leu Phe Asn Arg Lys Tyr Thr Thr Trp
                740                 745                 750

Asp Ser Leu Arg Gly Leu Tyr Ser Tyr Ser Thr Thr Asn Ala Val Asp
                755                 760                 765

Arg Asp Gly Lys Gly Leu Asp Arg Tyr Arg Ala Pro Gly Arg Asn Tyr
                770                 775                 780

Ala Val Ser Leu Glu Trp Lys Phe
785                 790

<210> SEQ ID NO 8
<211> LENGTH: 793
<212> TYPE: PRT
<213> ORGANISM: Neisseria meningitidis

<400> SEQUENCE: 8

Met Lys Pro Leu Gln Met Leu Pro Ile Ala Ala Leu Val Gly Ser Ile
1               5                   10                  15

Phe Gly Asn Pro Val Phe Ala Ala Asp Glu Ala Ala Thr Glu Thr Thr
                20                  25                  30

Pro Val Lys Ala Glu Val Lys Ala Val Arg Val Lys Gly Gln Arg Asn
                35                  40                  45

Ala Pro Ala Ala Val Glu Arg Val Asn Leu Asn Arg Ile Lys Gln Glu
                50                  55                  60

Met Ile Arg Asp Asn Lys Asp Leu Val Arg Tyr Ser Thr Asp Val Gly
65              70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
                100                 105                 110
```

```
Ser Glu Glu Asn Ser Leu Tyr Ala Arg Tyr Gly Asn Phe Asn Ser Ser
            115                 120                 125
Arg Leu Ser Ile Asp Pro Glu Leu Val Arg Asn Ile Asp Ile Val Lys
130                 135                 140
Gly Ala Asp Ser Phe Asn Thr Gly Ser Gly Ala Leu Gly Gly Gly Val
145                 150                 155                 160
Asn Tyr Gln Thr Leu Gln Gly Arg Asp Leu Leu Pro Glu Arg Gln
            165                 170                 175
Phe Gly Val Met Met Lys Asn Gly Tyr Ser Thr Arg Asn Arg Glu Trp
                180                 185                 190
Thr Asn Thr Leu Gly Phe Gly Val Ser Asn Asp Arg Val Asp Ala Ala
            195                 200                 205
Leu Leu Tyr Ser Gln Arg Arg Gly His Glu Thr Glu Ser Ala Gly Lys
210                 215                 220
Arg Gly Tyr Pro Val Glu Gly Ala Gly Ser Gly Ala Asn Ile Arg Gly
225                 230                 235                 240
Ser Ala Arg Gly Ile Pro Asp Pro Ser Gln His Lys Tyr Asn His His
                245                 250                 255
Ala Leu Gly Lys Ile Ala Tyr Gln Ile Asn Asp Asn His Arg Ile Gly
                260                 265                 270
Ala Ser Leu Asn Gly Gln Gln Gly His Asn Tyr Thr Val Glu Glu Ser
            275                 280                 285
Tyr Asn Leu Leu Ala Ser Tyr Trp Arg Glu Ala Asp Asp Val Asn Arg
            290                 295                 300
Arg Arg Asn Thr Asn Leu Phe Tyr Glu Trp Thr Pro Glu Ser Asp Arg
305                 310                 315                 320
Leu Ser Met Val Lys Ala Asp Val Asp Tyr Gln Lys Thr Lys Val Ser
                325                 330                 335
Ala Val Asn Tyr Lys Gly Ser Phe Pro Ile Glu Asp Ser Ser Thr Leu
            340                 345                 350
Thr Arg Asn Tyr Asn Gln Lys Asp Leu Asp Glu Ile Tyr Asn Arg Ser
            355                 360                 365
Met Asp Thr Arg Phe Lys Arg Ile Thr Leu Arg Leu Asp Ser His Pro
370                 375                 380
Leu Gln Leu Gly Gly Gly Arg His Arg Leu Ser Phe Lys Thr Phe Ala
385                 390                 395                 400
Ser Arg Arg Asp Phe Glu Asn Leu Asn Arg Asp Tyr Tyr Phe Ser
                405                 410                 415
Gly Arg Val Val Arg Thr Thr Ser Ser Ile Gln His Pro Val Lys Thr
            420                 425                 430
Thr Asn Tyr Gly Phe Ser Leu Ser Asp Gln Ile Gln Trp Asn Asp Val
            435                 440                 445
Phe Ser Ser Arg Ala Gly Ile Arg Tyr Asp His Thr Lys Met Thr Pro
450                 455                 460
Gln Glu Leu Asn Ala Glu Cys His Ala Cys Asp Lys Thr Pro Pro Ala
465                 470                 475                 480
Ala Asn Thr Tyr Lys Gly Trp Ser Gly Phe Val Gly Leu Ala Ala Gln
            485                 490                 495
Leu Asn Gln Ala Trp Arg Val Gly Tyr Asp Ile Thr Ser Gly Tyr Arg
            500                 505                 510
Val Pro Asn Ala Ser Glu Val Tyr Phe Thr Tyr Asn His Gly Ser Gly
            515                 520                 525
Asn Trp Leu Pro Asn Pro Asn Leu Lys Ala Glu Arg Thr Thr Thr His
```

```
            530                 535                 540
Thr Leu Ser Leu Gln Gly Arg Ser Glu Lys Gly Thr Leu Asp Ala Asn
545                 550                 555                 560

Leu Tyr Gln Ser Asn Tyr Arg Asn Phe Leu Ser Glu Glu Lys Leu
                565                 570                 575

Thr Thr Ser Gly Asp Val Ser Cys Thr Gln Met Asn Tyr Tyr Gly
                580                 585                 590

Met Cys Ser Asn Pro Tyr Ser Glu Lys Leu Glu Trp Gln Met Gln Asn
                595                 600                 605

Ile Asp Lys Ala Arg Ile Arg Gly Ile Glu Leu Thr Gly Arg Leu Asn
                610                 615                 620

Val Asp Lys Val Ala Ser Phe Val Pro Glu Gly Trp Lys Leu Phe Gly
625                 630                 635                 640

Ser Leu Gly Tyr Ala Lys Ser Lys Leu Ser Gly Asp Asn Ser Leu Leu
                645                 650                 655

Ser Thr Gln Pro Leu Lys Val Ile Ala Gly Ile Asp Tyr Glu Ser Pro
                660                 665                 670

Ser Glu Lys Trp Gly Val Phe Ser Arg Leu Thr Tyr Leu Gly Ala Lys
                675                 680                 685

Lys Val Lys Asp Ala Gln Tyr Thr Val Tyr Glu Asn Lys Gly Trp Gly
                690                 695                 700

Thr Pro Leu Gln Lys Lys Val Lys Asp Tyr Pro Trp Leu Asn Lys Ser
705                 710                 715                 720

Ala Tyr Val Phe Asp Met Tyr Gly Phe Tyr Lys Pro Val Lys Asn Leu
                725                 730                 735

Thr Leu Arg Ala Gly Val Tyr Asn Val Phe Asn Arg Lys Tyr Thr Thr
                740                 745                 750

Trp Asp Ser Leu Arg Gly Leu Tyr Ser Tyr Ser Thr Thr Asn Ser Val
                755                 760                 765

Asp Arg Asp Gly Lys Gly Leu Asp Arg Tyr Arg Ala Pro Ser Arg Asn
                770                 775                 780

Tyr Ala Val Ser Leu Glu Trp Lys Phe
785                 790

<210> SEQ ID NO 9
<211> LENGTH: 488
<212> TYPE: PRT
<213> ORGANISM: Neisseria meningitidis

<400> SEQUENCE: 9

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
                20                  25                  30

Thr Leu Ser Lys Pro Ala Ala Pro Val Val Ser Glu Lys Glu Thr Glu
                35                  40                  45

Ala Lys Glu Asp Ala Pro Gln Ala Gly Ser Gln Gly Gln Gly Ala Pro
                50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
                100                 105                 110
```

```
Thr Pro Asn His Thr Pro Asp Pro Asn Met Leu Ala Gly Asn Met Glu
            115                 120                 125
Asn Gln Ala Thr Asp Ala Gly Glu Ser Ser Gln Pro Ala Asn Gln Pro
        130                 135                 140
Asp Met Ala Asn Ala Ala Asp Gly Met Gln Gly Asp Pro Ser Ala
145                 150                 155                 160
Gly Gly Gln Asn Ala Gly Asn Thr Ala Ala Gln Gly Ala Asn Gln Ala
                165                 170                 175
Gly Asn Asn Gln Ala Ala Gly Ser Ser Asp Pro Ile Pro Ala Ser Asn
            180                 185                 190
Pro Ala Pro Ala Asn Gly Gly Ser Asn Phe Gly Arg Val Asp Leu Ala
        195                 200                 205
Asn Gly Val Leu Ile Asp Gly Pro Ser Gln Asn Ile Thr Leu Thr His
210                 215                 220
Cys Lys Gly Asp Ser Cys Ser Gly Asn Asn Phe Leu Asp Glu Glu Val
225                 230                 235                 240
Gln Leu Lys Ser Glu Phe Glu Lys Leu Ser Asp Ala Asp Lys Ile Ser
                245                 250                 255
Asn Tyr Lys Lys Asp Gly Lys Asn Asp Lys Phe Val Gly Leu Val Ala
            260                 265                 270
Asp Ser Val Gln Met Lys Gly Ile Asn Gln Tyr Ile Ile Phe Tyr Lys
        275                 280                 285
Pro Lys Pro Thr Ser Phe Ala Arg Phe Arg Arg Ser Ala Arg Ser Arg
290                 295                 300
Arg Ser Leu Pro Ala Glu Met Pro Leu Ile Pro Val Asn Gln Ala Asp
305                 310                 315                 320
Thr Leu Ile Val Asp Gly Glu Ala Val Ser Leu Thr Gly His Ser Gly
                325                 330                 335
Asn Ile Phe Ala Pro Glu Gly Asn Tyr Arg Tyr Leu Thr Tyr Gly Ala
            340                 345                 350
Glu Lys Leu Pro Gly Gly Ser Tyr Ala Leu Arg Val Gln Gly Glu Pro
        355                 360                 365
Ala Lys Gly Glu Met Leu Ala Gly Ala Ala Val Tyr Asn Gly Glu Val
370                 375                 380
Leu His Phe His Thr Glu Asn Gly Arg Pro Tyr Pro Thr Arg Gly Arg
385                 390                 395                 400
Phe Ala Ala Lys Val Asp Phe Gly Ser Lys Ser Val Asp Gly Ile Ile
                405                 410                 415
Asp Ser Gly Asp Asp Leu His Met Gly Thr Gln Lys Phe Lys Ala Ala
            420                 425                 430
Ile Asp Gly Asn Gly Phe Lys Gly Thr Trp Thr Glu Asn Gly Ser Gly
        435                 440                 445
Asp Val Ser Gly Lys Phe Tyr Gly Pro Ala Gly Glu Glu Val Ala Gly
450                 455                 460
Lys Tyr Ser Tyr Arg Pro Thr Asp Ala Glu Lys Gly Gly Phe Gly Val
465                 470                 475                 480
Phe Ala Gly Lys Lys Glu Gln Asp
                485

<210> SEQ ID NO 10
<211> LENGTH: 364
<212> TYPE: PRT
<213> ORGANISM: Neisseria meningitidis

<400> SEQUENCE: 10
```

```
Met Ser Met Lys His Phe Pro Ser Lys Val Leu Thr Ala Ile Leu
1               5                   10                  15

Ala Thr Phe Cys Ser Gly Ala Leu Ala Ala Thr Ser Asp Asp Val
            20                  25                  30

Lys Lys Ala Ala Thr Val Ala Ile Val Ala Ala Tyr Asn Asn Gly Gln
            35                  40                  45

Glu Ile Asn Gly Phe Lys Ala Gly Glu Thr Ile Tyr Asp Ile Gly Glu
50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
            85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
            115                 120                 125

Ala Ala Leu Ala Asp Thr Asp Ala Ala Leu Asp Glu Thr Thr Asn Ala
130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
            165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
            195                 200                 205

Lys Gln Thr Ala Glu Gly Thr Lys Gln Asn Val Asp Ala Lys Val Lys
            210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Lys Val Thr Asp
            245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
            275                 280                 285

Thr Arg Gln Gly Leu Ala Glu Gln Ala Ala Leu Ser Gly Leu Phe Gln
            290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
            325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
            355                 360
```

<210> SEQ ID NO 11
<211> LENGTH: 174
<212> TYPE: PRT
<213> ORGANISM: Neisseria meningitidis

<400> SEQUENCE: 11

Met Lys Lys Ala Leu Ala Thr Leu Ile Ala Leu Ala Leu Pro Ala Ala

```
                 1               5                  10                 15
             Ala Leu Ala Glu Gly Ala Ser Gly Phe Tyr Val Gln Ala Asp Ala Ala
                            20                  25                  30

His Ala Lys Ala Ser Ser Leu Gly Ser Ala Lys Gly Phe Ser Pro
                         35                  40                  45

Arg Ile Ser Ala Gly Tyr Arg Ile Asn Asp Leu Arg Phe Ala Val Asp
                         50                  55                  60

Tyr Thr Arg Tyr Lys Asn Tyr Lys Ala Pro Ser Thr Asp Phe Lys Leu
              65                  70                  75                  80

Tyr Ser Ile Gly Ala Ser Ala Ile Tyr Asp Phe Asp Thr Gln Ser Pro
                             85                  90                  95

Val Lys Pro Tyr Leu Gly Ala Arg Leu Ser Leu Asn Arg Ala Ser Val
                            100                 105                 110

Asp Leu Gly Gly Ser Asp Ser Phe Ser Gln Thr Ser Ile Gly Leu Gly
                            115                 120                 125

Val Leu Thr Gly Val Ser Tyr Ala Val Thr Pro Asn Val Asp Leu Asp
                         130                 135                 140

Ala Gly Tyr Arg Tyr Asn Tyr Ile Gly Lys Val Asn Thr Val Lys Asn
             145                 150                 155                 160

Val Arg Ser Gly Glu Leu Ser Ala Gly Val Arg Val Lys Phe
                            165                 170

<210> SEQ ID NO 12
<211> LENGTH: 591
<212> TYPE: PRT
<213> ORGANISM: Neisseria meningitidis

<400> SEQUENCE: 12

Met Asn Lys Ile Tyr Arg Ile Ile Trp Asn Ser Ala Leu Asn Ala Trp
 1               5                  10                  15

Val Val Val Ser Glu Leu Thr Arg Asn His Thr Lys Arg Ala Ser Ala
                20                  25                  30

Thr Val Lys Thr Ala Val Leu Ala Thr Leu Phe Ala Thr Val Gln
             35                  40                  45

Ala Ser Ala Asn Asn Glu Glu Gln Glu Glu Asp Leu Tyr Leu Asp Pro
         50                  55                  60

Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
             115                 120                 125

Leu Lys Lys Asp Leu Thr Asp Leu Thr Ser Val Gly Thr Glu Lys Leu
         130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
                180                 185                 190

Thr Gly Ala Thr Thr Asn Val Thr Asn Asp Asn Val Thr Asp Asp Glu
             195                 200                 205
```

```
Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Gln Gly Asn Ile
            355                 360                 365

Thr Val Met Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
                420                 425                 430

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
        450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
        515                 520                 525

Gly Leu Val Gln Ala Tyr Leu Pro Gly Lys Ser Met Met Ala Ile Gly
530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590
```

<210> SEQ ID NO 13
<211> LENGTH: 1457
<212> TYPE: PRT
<213> ORGANISM: Neisseria meningitidis

<400> SEQUENCE: 13

```
Met Lys Thr Thr Asp Lys Arg Thr Thr Glu Thr His Arg Lys Ala Pro
1               5                   10                  15
Lys Thr Gly Arg Ile Arg Phe Ser Pro Ala Tyr Leu Ala Ile Cys Leu
            20                  25                  30
Ser Phe Gly Ile Leu Pro Gln Ala Trp Ala Gly His Thr Tyr Phe Gly
        35                  40                  45
Ile Asn Tyr Gln Tyr Tyr Arg Asp Phe Ala Glu Asn Lys Gly Lys Phe
    50                  55                  60
Ala Val Gly Ala Lys Asp Ile Glu Val Tyr Asn Lys Lys Gly Glu Leu
65                  70                  75                  80
Val Gly Lys Ser Met Thr Lys Ala Pro Met Ile Asp Phe Ser Val Val
                85                  90                  95
Ser Arg Asn Gly Val Ala Ala Leu Val Gly Asp Gln Tyr Ile Val Ser
                100                 105                 110
Val Ala His Asn Gly Gly Tyr Asn Asn Val Asp Phe Gly Ala Glu Gly
        115                 120                 125
Arg Asn Pro Asp Gln His Arg Phe Thr Tyr Lys Ile Val Lys Arg Asn
    130                 135                 140
Asn Tyr Lys Ala Gly Thr Lys Gly His Pro Tyr Gly Gly Asp Tyr His
145                 150                 155                 160
Met Pro Arg Leu His Lys Phe Val Thr Asp Ala Glu Pro Val Glu Met
                165                 170                 175
Thr Ser Tyr Met Asp Gly Arg Lys Tyr Ile Asp Gln Asn Asn Tyr Pro
                180                 185                 190
Asp Arg Val Arg Ile Gly Ala Gly Arg Gln Tyr Trp Arg Ser Asp Glu
            195                 200                 205
Asp Glu Pro Asn Asn Arg Glu Ser Ser Tyr His Ile Ala Ser Ala Tyr
        210                 215                 220
Ser Trp Leu Val Gly Gly Asn Thr Phe Ala Gln Asn Gly Ser Gly Gly
225                 230                 235                 240
Gly Thr Val Asn Leu Gly Ser Glu Lys Ile Lys His Ser Pro Tyr Gly
                245                 250                 255
Phe Leu Pro Thr Gly Gly Ser Phe Gly Asp Ser Gly Ser Pro Met Phe
                260                 265                 270
Ile Tyr Asp Ala Gln Lys Gln Lys Trp Leu Ile Asn Gly Val Leu Gln
            275                 280                 285
Thr Gly Asn Pro Tyr Ile Gly Lys Ser Asn Gly Phe Gln Leu Val Arg
        290                 295                 300
Lys Asp Trp Phe Tyr Asp Glu Ile Phe Ala Gly Asp Thr His Ser Val
305                 310                 315                 320
Phe Tyr Glu Pro Arg Gln Asn Gly Lys Tyr Ser Phe Asn Asp Asp Asn
                325                 330                 335
Asn Gly Thr Gly Lys Ile Asn Ala Lys His Glu His Asn Ser Leu Pro
            340                 345                 350
Asn Arg Leu Lys Thr Arg Thr Val Gln Leu Phe Asn Val Ser Leu Ser
        355                 360                 365
Glu Thr Ala Arg Glu Pro Val Tyr His Ala Ala Gly Val Asn Ser
    370                 375                 380
Tyr Arg Pro Arg Leu Asn Asn Gly Glu Asn Ile Ser Phe Ile Asp Glu
385                 390                 395                 400
Gly Lys Gly Glu Leu Ile Leu Thr Ser Asn Ile Asn Gln Gly Ala Gly
                405                 410                 415
```

```
Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
        675                 680                 685

Gly Gly Gln Ala Val Val Ser Arg Asn Val Ala Lys Val Lys Gly Asp
    690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
            740                 745                 750

Lys Thr Asp Ile Ser Gly Asn Val Asp Leu Ala Asp His Ala His Leu
        755                 760                 765

Asn Leu Thr Gly Leu Ala Thr Leu Asn Gly Asn Leu Ser Ala Asn Gly
    770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
```

```
                835                 840                 845
Val Ser His Ser Ala Leu Asn Gly Asn Val Ser Leu Ala Asp Lys Ala
850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
                900                 905                 910

Asn Ser Ala Tyr Arg His Asp Ala Ala Gly Ala Gln Thr Gly Ser Ala
                915                 920                 925

Thr Asp Ala Pro Arg Arg Ser Arg Arg Ser Arg Arg Ser Leu Leu
930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                965                 970                 975

Leu Phe Gly Tyr Arg Ser Asp Lys Leu Lys Leu Ala Glu Ser Ser Glu
                980                 985                 990

Gly Thr Tyr Thr Leu Ala Val Asn Asn Thr Gly Asn Glu Pro Ala Ser
                995                 1000                1005

Leu Glu Gln Leu Thr Val Val Glu Gly Lys Asp Asn Lys Pro Leu Ser
                1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
                1045                1050                1055

Pro Val Lys Glu Gln Glu Leu Ser Asp Lys Leu Gly Lys Ala Glu Ala
                1060                1065                1070

Lys Lys Gln Ala Glu Lys Asp Asn Ala Gln Ser Leu Asp Ala Leu Ile
                1075                1080                1085

Ala Ala Gly Arg Asp Ala Val Glu Lys Thr Glu Ser Val Ala Glu Pro
1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
                1125                1130                1135

Arg Glu Ala Glu Thr Arg Pro Ala Thr Thr Ala Phe Pro Arg Ala Arg
                1140                1145                1150

Arg Ala Arg Arg Asp Leu Pro Gln Leu Gln Pro Gln Pro Gln
                1155                1160                1165

Pro Gln Arg Asp Leu Ile Ser Arg Tyr Ala Asn Ser Gly Leu Ser Glu
                1170                1175                1180

Phe Ser Ala Thr Leu Asn Ser Val Phe Ala Val Gln Asp Glu Leu Asp
1185                1190                1195                1200

Arg Val Phe Ala Glu Asp Arg Arg Asn Ala Val Trp Thr Ser Gly Ile
                1205                1210                1215

Arg Asp Thr Lys His Tyr Arg Ser Gln Asp Phe Arg Ala Tyr Arg Gln
                1220                1225                1230

Gln Thr Asp Leu Arg Gln Ile Gly Met Gln Lys Asn Leu Gly Ser Gly
                1235                1240                1245

Arg Val Gly Ile Leu Phe Ser His Asn Arg Thr Glu Asn Thr Phe Asp
                1250                1255                1260
```

-continued

```
Asp Gly Ile Gly Asn Ser Ala Arg Leu Ala His Gly Ala Val Phe Gly
1265                1270                1275                1280

Gln Tyr Gly Ile Asp Arg Phe Tyr Ile Gly Ile Ser Ala Gly Ala Gly
            1285                1290                1295

Phe Ser Ser Gly Ser Leu Ser Asp Gly Ile Gly Gly Lys Ile Arg Arg
        1300                1305                1310

Arg Val Leu His Tyr Gly Ile Gln Ala Arg Tyr Arg Ala Gly Phe Gly
    1315                1320                1325

Gly Phe Gly Ile Glu Pro His Ile Gly Ala Thr Arg Tyr Phe Val Gln
1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
            1365                1370                1375

Pro Ala Gln His Ile Ser Ile Thr Pro Tyr Leu Ser Leu Ser Tyr Thr
        1380                1385                1390

Asp Ala Ala Ser Gly Lys Val Arg Thr Arg Val Asn Thr Ala Val Leu
    1395                1400                1405

Ala Gln Asp Phe Gly Lys Thr Arg Ser Ala Glu Trp Gly Val Asn Ala
    1410                1415                1420

Glu Ile Lys Gly Phe Thr Leu Ser Leu His Ala Ala Ala Lys Gly
1425                1430                1435                1440

Pro Gln Leu Glu Ala Gln His Ser Ala Gly Ile Lys Leu Gly Tyr Arg
            1445                1450                1455

Trp

<210> SEQ ID NO 14
<211> LENGTH: 797
<212> TYPE: PRT
<213> ORGANISM: Neisseria meningitidis

<400> SEQUENCE: 14

Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175
```

```
Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asn Gln Phe Asn Glu Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
    290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
        355                 360                 365

Leu Arg Gln Met Glu Ser Ala Pro Tyr Asp Thr Ser Lys Leu Gln Arg
    370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
            420                 425                 430

Val Gln Asp Thr Gly Leu Val Met Ser Ala Gly Val Ser Gln Asp Asn
        435                 440                 445

Leu Phe Gly Thr Gly Lys Ser Ala Ala Leu Arg Ala Ser Arg Ser Lys
    450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Val Tyr Gly Lys Ala Phe Asp Pro
                485                 490                 495

Arg Lys Ala Ser Thr Ser Ile Lys Gln Tyr Lys Thr Thr Thr Ala Gly
            500                 505                 510

Ala Gly Ile Arg Met Ser Val Pro Val Thr Glu Tyr Asp Arg Val Asn
        515                 520                 525

Phe Gly Leu Val Ala Glu His Leu Thr Val Asn Thr Tyr Asn Lys Ala
    530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Gly Tyr Leu
            580                 585                 590
```

```
Thr Gly Val Asn Ala Glu Ile Ala Leu Pro Gly Ser Lys Leu Gln Tyr
            595                 600                 605

Tyr Ser Ala Thr His Asn Gln Thr Trp Phe Phe Pro Leu Ser Lys Thr
        610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Leu
                645                 650                 655

Gly Ser Val Arg Gly Tyr Glu Ser Gly Thr Leu Gly Pro Lys Val Tyr
                660                 665                 670

Asp Glu Tyr Gly Glu Lys Ile Ser Tyr Gly Asn Lys Lys Ala Asn
                675                 680                 685

Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ala Thr Gly Gly Arg Val Gln
                725                 730                 735

Asn Ile Tyr Gly Ala Gly Asn Thr His Lys Ser Thr Phe Thr Asn Glu
                740                 745                 750

Leu Arg Tyr Ser Ala Gly Gly Ala Val Thr Trp Leu Ser Pro Leu Gly
                755                 760                 765

Pro Met Lys Phe Ser Tyr Ala Tyr Pro Leu Lys Lys Lys Pro Glu Asp
770                 775                 780

Glu Ile Gln Arg Phe Gln Phe Gln Leu Gly Thr Thr Phe
785                 790                 795

<210> SEQ ID NO 15
<211> LENGTH: 6
<212> TYPE: PRT
<213> ORGANISM: Artificial Sequence
<220> FEATURE:
<223> OTHER INFORMATION: Linker

<400> SEQUENCE: 15

Gly Ser Gly Gly Gly Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Linker

<400> SEQUENCE: 16

Gly Ser Gly Ser Gly Gly Gly Gly
1               5

<210> SEQ ID NO 17
<211> LENGTH: 18
<212> TYPE: DNA
<213> ORGANISM: Neisseria meningitidis

<400> SEQUENCE: 17
tttgcggggg ggggggggg                                               18

<210> SEQ ID NO 18
<211> LENGTH: 35
<212> TYPE: DNA
```

<213> ORGANISM: Neisseria meningitidis

<400> SEQUENCE: 18
ttgacaggcg aaggaatac tttataattc gcaac                           35

<210> SEQ ID NO 19
<211> LENGTH: 791
<212> TYPE: PRT
<213> ORGANISM: Neisseria meningitidis

<400> SEQUENCE: 19

```
Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
            20                  25                  30

Pro Val Lys Ala Glu Ile Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Glu Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Leu Asp Asp Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Asn
    210                 215                 220

Arg Gly Tyr Ala Val Glu Gly Glu Gly Ser Gly Ala Asn Ile Arg Gly
225                 230                 235                 240

Ser Ala Arg Gly Ile Pro Asp Ser Ser Lys His Lys Tyr His Ser Phe
                245                 250                 255

Leu Gly Lys Ile Ala Tyr Gln Ile Asn Asp Asn His Arg Ile Gly Ala
            260                 265                 270

Ser Leu Asn Gly Gln Gln Gly His Asn Tyr Thr Val Glu Glu Ser Tyr
        275                 280                 285

Asn Leu Thr Ala Ser Ser Trp Arg Glu Ala Asp Asp Val Asn Arg Arg
    290                 295                 300

Arg Asn Ala Asn Leu Phe Tyr Glu Trp Met Pro Asp Ser Asn Trp Leu
305                 310                 315                 320

Ser Ser Leu Lys Ala Asp Phe Asp Tyr Gln Lys Thr Lys Val Ala Ala
                325                 330                 335

Val Asn Asn Lys Gly Ser Phe Pro Met Asp Tyr Ser Thr Trp Thr Arg
            340                 345                 350
```

-continued

```
Asn Tyr Asn Gln Lys Asp Leu Asp Glu Ile Tyr Asn Arg Ser Met Asp
            355                 360                 365

Thr Arg Phe Lys Arg Phe Thr Leu Arg Leu Asp Ser His Pro Leu Gln
370                 375                 380

Leu Gly Gly Arg His Arg Leu Ser Phe Lys Thr Phe Val Ser Arg
385                 390                 395                 400

Arg Asp Phe Glu Asn Leu Asn Arg Asp Tyr Tyr Phe Ser Gly Arg
                405                 410                 415

Val Val Arg Thr Thr Ser Ser Ile Gln His Pro Val Lys Thr Thr Asn
            420                 425                 430

Tyr Gly Phe Ser Leu Ser Asp Gln Ile Gln Trp Asn Asp Val Phe Ser
            435                 440                 445

Ser Arg Ala Gly Ile Arg Tyr Asp His Thr Lys Met Thr Pro Gln Glu
            450                 455                 460

Leu Asn Ala Glu Cys His Ala Cys Asp Lys Thr Pro Pro Ala Ala Asn
465                 470                 475                 480

Thr Tyr Lys Gly Trp Ser Gly Phe Val Gly Leu Ala Ala Gln Leu Asn
                485                 490                 495

Gln Ala Trp His Val Gly Tyr Asp Ile Thr Ser Gly Tyr Arg Val Pro
            500                 505                 510

Asn Ala Ser Glu Val Tyr Phe Thr Tyr Asn His Gly Ser Gly Asn Trp
            515                 520                 525

Leu Pro Asn Pro Asn Leu Lys Ala Glu Arg Ser Thr Thr His Thr Leu
530                 535                 540

Ser Leu Gln Gly Arg Ser Glu Lys Gly Met Leu Asp Ala Asn Leu Tyr
545                 550                 555                 560

Gln Ser Asn Tyr Arg Asn Phe Leu Ser Glu Glu Gln Lys Leu Thr Thr
                565                 570                 575

Ser Gly Thr Pro Gly Cys Thr Glu Glu Asn Ala Tyr Tyr Gly Ile Cys
            580                 585                 590

Ser Asp Pro Tyr Lys Glu Lys Leu Asp Trp Gln Met Lys Asn Ile Asp
            595                 600                 605

Lys Ala Arg Ile Arg Gly Ile Glu Leu Thr Gly Arg Leu Asn Val Asp
            610                 615                 620

Lys Val Ala Ser Phe Val Pro Glu Gly Trp Lys Leu Phe Gly Ser Leu
625                 630                 635                 640

Gly Tyr Ala Lys Ser Lys Leu Ser Gly Asp Asn Ser Leu Leu Ser Thr
                645                 650                 655

Gln Pro Leu Lys Val Ile Ala Gly Ile Asp Tyr Glu Ser Pro Ser Glu
            660                 665                 670

Lys Trp Gly Val Phe Ser Arg Leu Thr Tyr Leu Gly Ala Lys Lys Ala
            675                 680                 685

Lys Asp Ala Gln Tyr Thr Val Tyr Glu Asn Lys Gly Trp Gly Thr Pro
            690                 695                 700

Leu Gln Lys Lys Val Lys Asp Tyr Pro Trp Leu Asn Lys Ser Ala Tyr
705                 710                 715                 720

Val Phe Asp Met Tyr Gly Phe Tyr Lys Pro Ala Lys Asn Leu Thr Leu
                725                 730                 735

Arg Ala Gly Val Tyr Asn Val Phe Asn Arg Lys Tyr Thr Thr Trp Asp
            740                 745                 750

Ser Leu Arg Gly Leu Tyr Ser Tyr Ser Thr Thr Asn Ser Val Asp Arg
            755                 760                 765
```

```
Asp Gly Lys Gly Leu Asp Arg Tyr Arg Ala Pro Ser Arg Asn Tyr Ala
        770                 775                 780

Val Ser Leu Glu Trp Lys Phe
785                 790

<210> SEQ ID NO 20
<211> LENGTH: 147
<212> TYPE: PRT
<213> ORGANISM: Neisseria meningitidis

<400> SEQUENCE: 20

Ala Asp Glu Ala Ala Thr Glu Thr Thr Pro Val Lys Ala Glu Ile Lys
1               5                   10                  15

Ala Val Arg Val Lys Gly Gln Arg Asn Ala Pro Ala Ala Val Glu Arg
            20                  25                  30

Val Asn Leu Asn Arg Ile Lys Gln Glu Met Ile Arg Asp Asn Lys Asp
        35                  40                  45

Leu Val Arg Tyr Ser Thr Asp Val Gly Leu Ser Asp Ser Gly Arg His
    50                  55                  60

Gln Lys Gly Phe Ala Val Arg Gly Val Glu Gly Asn Arg Val Gly Val
65                  70                  75                  80

Ser Ile Asp Gly Val Asn Leu Pro Asp Ser Glu Asn Ser Leu Tyr
                85                  90                  95

Ala Arg Tyr Gly Asn Phe Asn Ser Ser Arg Leu Ser Ile Asp Pro Glu
            100                 105                 110

Leu Val Arg Asn Ile Glu Ile Val Lys Gly Ala Asp Ser Phe Asn Thr
        115                 120                 125

Gly Ser Gly Ala Leu Gly Gly Val Asn Tyr Gln Thr Leu Gln Gly
    130                 135                 140

Arg Asp Leu
145

<210> SEQ ID NO 21
<211> LENGTH: 621
<212> TYPE: PRT
<213> ORGANISM: Neisseria meningitidis

<400> SEQUENCE: 21

Leu Leu Asp Asp Arg Gln Phe Gly Val Met Met Lys Asn Gly Tyr Ser
1               5                   10                  15

Thr Arg Asn Arg Glu Trp Thr Asn Thr Leu Gly Phe Gly Val Ser Asn
            20                  25                  30

Asp Arg Val Asp Ala Ala Leu Leu Tyr Ser Gln Arg Gly His Glu
        35                  40                  45

Thr Glu Ser Ala Gly Asn Arg Gly Tyr Ala Val Glu Gly Glu Gly Ser
    50                  55                  60

Gly Ala Asn Ile Arg Gly Ser Ala Arg Gly Ile Pro Asp Ser Ser Lys
65                  70                  75                  80

His Lys Tyr His Ser Phe Leu Gly Lys Ile Ala Tyr Gln Ile Asn Asp
                85                  90                  95

Asn His Arg Ile Gly Ala Ser Leu Asn Gly Gln Gln Gly His Asn Tyr
            100                 105                 110

Thr Val Glu Glu Ser Tyr Asn Leu Thr Ala Ser Ser Trp Arg Glu Ala
        115                 120                 125

Asp Asp Val Asn Arg Arg Arg Asn Ala Asn Leu Phe Tyr Glu Trp Met
    130                 135                 140
```

```
Pro Asp Ser Asn Trp Leu Ser Ser Leu Lys Ala Asp Phe Asp Tyr Gln
145                 150                 155                 160

Lys Thr Lys Val Ala Ala Val Asn Asn Lys Gly Ser Phe Pro Met Asp
            165                 170                 175

Tyr Ser Thr Trp Thr Arg Asn Tyr Asn Gln Lys Asp Leu Asp Glu Ile
                180                 185                 190

Tyr Asn Arg Ser Met Asp Thr Arg Phe Lys Arg Phe Thr Leu Arg Leu
            195                 200                 205

Asp Ser His Pro Leu Gln Leu Gly Gly Arg His Arg Leu Ser Phe
            210                 215                 220

Lys Thr Phe Val Ser Arg Arg Asp Phe Glu Asn Leu Asn Arg Asp Asp
225                 230                 235                 240

Tyr Tyr Phe Ser Gly Arg Val Val Arg Thr Thr Ser Ser Ile Gln His
                245                 250                 255

Pro Val Lys Thr Thr Asn Tyr Gly Phe Ser Leu Ser Asp Gln Ile Gln
            260                 265                 270

Trp Asn Asp Val Phe Ser Ser Arg Ala Gly Ile Arg Tyr Asp His Thr
            275                 280                 285

Lys Met Thr Pro Gln Glu Leu Asn Ala Glu Cys His Ala Cys Asp Lys
290                 295                 300

Thr Pro Pro Ala Ala Asn Thr Tyr Lys Gly Trp Ser Gly Phe Val Gly
305                 310                 315                 320

Leu Ala Ala Gln Leu Asn Gln Ala Trp His Val Gly Tyr Asp Ile Thr
                325                 330                 335

Ser Gly Tyr Arg Val Pro Asn Ala Ser Glu Val Tyr Phe Thr Tyr Asn
            340                 345                 350

His Gly Ser Gly Asn Trp Leu Pro Asn Pro Asn Leu Lys Ala Glu Arg
            355                 360                 365

Ser Thr Thr His Thr Leu Ser Leu Gln Gly Arg Ser Glu Lys Gly Met
            370                 375                 380

Leu Asp Ala Asn Leu Tyr Gln Ser Asn Tyr Arg Asn Phe Leu Ser Glu
385                 390                 395                 400

Glu Gln Lys Leu Thr Thr Ser Gly Thr Pro Gly Cys Thr Glu Asn
                405                 410                 415

Ala Tyr Tyr Gly Ile Cys Ser Asp Pro Tyr Lys Glu Lys Leu Asp Trp
            420                 425                 430

Gln Met Lys Asn Ile Asp Lys Ala Arg Ile Arg Gly Ile Glu Leu Thr
            435                 440                 445

Gly Arg Leu Asn Val Asp Lys Val Ala Ser Phe Val Pro Glu Gly Trp
450                 455                 460

Lys Leu Phe Gly Ser Leu Gly Tyr Ala Lys Ser Lys Leu Ser Gly Asp
465                 470                 475                 480

Asn Ser Leu Leu Ser Thr Gln Pro Leu Lys Val Ile Ala Gly Ile Asp
                485                 490                 495

Tyr Glu Ser Pro Ser Glu Lys Trp Gly Val Phe Ser Arg Leu Thr Tyr
            500                 505                 510

Leu Gly Ala Lys Lys Ala Lys Asp Ala Gln Tyr Thr Val Tyr Glu Asn
            515                 520                 525

Lys Gly Trp Gly Thr Pro Leu Gln Lys Val Lys Asp Tyr Pro Trp
            530                 535                 540

Leu Asn Lys Ser Ala Tyr Val Phe Asp Met Tyr Gly Phe Tyr Lys Pro
545                 550                 555                 560

Ala Lys Asn Leu Thr Leu Arg Ala Gly Val Tyr Asn Val Phe Asn Arg
```

```
                565                 570                 575
Lys Tyr Thr Thr Trp Asp Ser Leu Arg Gly Leu Tyr Ser Tyr Ser Thr
            580                 585                 590

Thr Asn Ser Val Asp Arg Asp Gly Lys Gly Leu Asp Arg Tyr Arg Ala
            595                 600                 605

Pro Ser Arg Asn Tyr Ala Val Ser Leu Glu Trp Lys Phe
    610                 615                 620

<210> SEQ ID NO 22
<211> LENGTH: 768
<212> TYPE: PRT
<213> ORGANISM: Neisseria meningitidis

<400> SEQUENCE: 22

Ala Asp Glu Ala Ala Thr Glu Thr Thr Pro Val Lys Ala Glu Ile Lys
1               5                   10                  15

Ala Val Arg Val Lys Gly Gln Arg Asn Ala Pro Ala Ala Val Glu Arg
            20                  25                  30

Val Asn Leu Asn Arg Ile Lys Gln Glu Met Ile Arg Asp Asn Lys Asp
        35                  40                  45

Leu Val Arg Tyr Ser Thr Asp Val Gly Leu Ser Asp Ser Gly Arg His
    50                  55                  60

Gln Lys Gly Phe Ala Val Arg Gly Val Glu Gly Asn Arg Val Gly Val
65              70                  75                  80

Ser Ile Asp Gly Val Asn Leu Pro Asp Ser Glu Glu Asn Ser Leu Tyr
            85                  90                  95

Ala Arg Tyr Gly Asn Phe Asn Ser Ser Arg Leu Ser Ile Asp Pro Glu
            100                 105                 110

Leu Val Arg Asn Ile Glu Ile Val Lys Gly Ala Asp Ser Phe Asn Thr
        115                 120                 125

Gly Ser Gly Ala Leu Gly Gly Val Asn Tyr Gln Thr Leu Gln Gly
    130                 135                 140

Arg Asp Leu Leu Leu Asp Asp Arg Gln Phe Gly Val Met Met Lys Asn
145                 150                 155                 160

Gly Tyr Ser Thr Arg Asn Arg Glu Trp Thr Asn Thr Leu Gly Phe Gly
            165                 170                 175

Val Ser Asn Asp Arg Val Asp Ala Ala Leu Leu Tyr Ser Gln Arg Arg
            180                 185                 190

Gly His Glu Thr Glu Ser Ala Gly Asn Arg Gly Tyr Ala Val Glu Gly
        195                 200                 205

Glu Gly Ser Gly Ala Asn Ile Arg Gly Ser Ala Arg Gly Ile Pro Asp
    210                 215                 220

Ser Ser Lys His Lys Tyr His Ser Phe Leu Gly Lys Ile Ala Tyr Gln
225                 230                 235                 240

Ile Asn Asp Asn His Arg Ile Gly Ala Ser Leu Asn Gly Gln Gln Gly
            245                 250                 255

His Asn Tyr Thr Val Glu Glu Ser Tyr Asn Leu Thr Ala Ser Ser Trp
            260                 265                 270

Arg Glu Ala Asp Asp Val Asn Arg Arg Arg Asn Ala Asn Leu Phe Tyr
        275                 280                 285

Glu Trp Met Pro Asp Ser Asn Trp Leu Ser Ser Leu Lys Ala Asp Phe
    290                 295                 300

Asp Tyr Gln Lys Thr Lys Val Ala Ala Val Asn Asn Lys Gly Ser Phe
305                 310                 315                 320
```

Pro Met Asp Tyr Ser Thr Trp Thr Arg Asn Tyr Asn Gln Lys Asp Leu
              325                 330                 335

Asp Glu Ile Tyr Asn Arg Ser Met Asp Thr Arg Phe Lys Arg Phe Thr
          340                 345                 350

Leu Arg Leu Asp Ser His Pro Leu Gln Leu Gly Gly Gly Arg His Arg
      355                 360                 365

Leu Ser Phe Lys Thr Phe Val Ser Arg Arg Asp Phe Glu Asn Leu Asn
  370                 375                 380

Arg Asp Asp Tyr Tyr Phe Ser Gly Arg Val Val Arg Thr Thr Ser Ser
385                 390                 395                 400

Ile Gln His Pro Val Lys Thr Thr Asn Tyr Gly Phe Ser Leu Ser Asp
              405                 410                 415

Gln Ile Gln Trp Asn Asp Val Phe Ser Ser Arg Ala Gly Ile Arg Tyr
          420                 425                 430

Asp His Thr Lys Met Thr Pro Gln Glu Leu Asn Ala Glu Cys His Ala
      435                 440                 445

Cys Asp Lys Thr Pro Pro Ala Ala Asn Thr Tyr Lys Gly Trp Ser Gly
  450                 455                 460

Phe Val Gly Leu Ala Ala Gln Leu Asn Gln Ala Trp His Val Gly Tyr
465                 470                 475                 480

Asp Ile Thr Ser Gly Tyr Arg Val Pro Asn Ala Ser Glu Val Tyr Phe
              485                 490                 495

Thr Tyr Asn His Gly Ser Gly Asn Trp Leu Pro Asn Pro Asn Leu Lys
          500                 505                 510

Ala Glu Arg Ser Thr Thr His Thr Leu Ser Leu Gln Gly Arg Ser Glu
      515                 520                 525

Lys Gly Met Leu Asp Ala Asn Leu Tyr Gln Ser Asn Tyr Arg Asn Phe
  530                 535                 540

Leu Ser Glu Glu Gln Lys Leu Thr Thr Ser Gly Thr Pro Gly Cys Thr
545                 550                 555                 560

Glu Glu Asn Ala Tyr Tyr Gly Ile Cys Ser Asp Pro Tyr Lys Glu Lys
              565                 570                 575

Leu Asp Trp Gln Met Lys Asn Ile Asp Lys Ala Arg Ile Arg Gly Ile
          580                 585                 590

Glu Leu Thr Gly Arg Leu Asn Val Asp Lys Val Ala Ser Phe Val Pro
      595                 600                 605

Glu Gly Trp Lys Leu Phe Gly Ser Leu Gly Tyr Ala Lys Ser Lys Leu
  610                 615                 620

Ser Gly Asp Asn Ser Leu Leu Ser Thr Gln Pro Leu Lys Val Ile Ala
625                 630                 635                 640

Gly Ile Asp Tyr Glu Ser Pro Ser Glu Lys Trp Gly Val Phe Ser Arg
              645                 650                 655

Leu Thr Tyr Leu Gly Ala Lys Lys Ala Lys Asp Ala Gln Tyr Thr Val
          660                 665                 670

Tyr Glu Asn Lys Gly Trp Gly Thr Pro Leu Gln Lys Lys Val Lys Asp
      675                 680                 685

Tyr Pro Trp Leu Asn Lys Ser Ala Tyr Val Phe Asp Met Tyr Gly Phe
  690                 695                 700

Tyr Lys Pro Ala Lys Asn Leu Thr Leu Arg Ala Gly Val Tyr Asn Val
705                 710                 715                 720

Phe Asn Arg Lys Tyr Thr Thr Trp Asp Ser Leu Arg Gly Leu Tyr Ser
              725                 730                 735

Tyr Ser Thr Thr Asn Ser Val Asp Arg Asp Gly Lys Gly Leu Asp Arg

```
                    740                 745                 750
Tyr Arg Ala Pro Ser Arg Asn Tyr Ala Val Ser Leu Glu Trp Lys Phe
            755                 760                 765

<210> SEQ ID NO 23
<211> LENGTH: 915
<212> TYPE: PRT
<213> ORGANISM: Neisseria meningitidis

<400> SEQUENCE: 23

Met Gln Gln Gln His Leu Phe Arg Phe Asn Ile Leu Cys Leu Ser Leu
1               5                   10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Ser
    50                  55                  60

Ser Asp Thr Leu Ser Lys Glu Gln Val Leu Asn Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Val Ser Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Ile Ala
        195                 200                 205

Leu Ala Gly Arg Ile Gly Gly Ala Glu Ala Leu Leu Ile His Thr Gly
    210                 215                 220

Arg Arg Ala Gly Glu Ile Arg Ala His Glu Asp Ala Gly Arg Gly Val
225                 230                 235                 240

Gln Ser Phe Asn Arg Leu Val Pro Val Glu Asp Ser Ser Asn Tyr Ala
                245                 250                 255

Tyr Phe Ile Val Lys Glu Glu Cys Lys Asn Gly Ser Tyr Glu Thr Cys
            260                 265                 270

Lys Ala Asn Pro Lys Lys Asp Val Val Gly Lys Asp Glu Arg Gln Thr
        275                 280                 285

Val Ser Thr Arg Asp Tyr Thr Gly Pro Asn Arg Phe Leu Ala Asp Pro
    290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu His Thr Gln Gln
                325                 330                 335

Thr Phe Asp Thr Arg Asp Met Thr Val Pro Ala Phe Leu Thr Lys Ala
            340                 345                 350
```

-continued

```
Val Phe Asp Ala Asn Lys Lys Gln Ala Gly Ser Leu Pro Gly Asn Gly
            355                 360                 365

Lys Tyr Ala Gly Asn His Lys Tyr Gly Gly Leu Phe Thr Asn Gly Glu
    370                 375                 380

Asn Gly Ala Leu Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
            420                 425                 430

Gln Gly Ile Gly Leu Asp Asn His Phe Gln Gln Thr His Cys Ser Ala
        435                 440                 445

Asp Gly Ser Asp Lys Tyr Cys Arg Pro Ser Ala Asp Lys Pro Phe Ser
    450                 455                 460

Tyr Tyr Lys Ser Asp Arg Val Ile Tyr Gly Glu Ser His Arg Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Phe Asp Arg Phe Gly Ser Asn Leu Arg His
            500                 505                 510

Gln Asp Tyr Tyr Tyr Gln His Ala Asn Arg Ala Tyr Ser Ser Asn Thr
        515                 520                 525

Pro Pro Gln Asn Asn Gly Lys Lys Ile Ser Pro Asn Gly Ser Glu Thr
    530                 535                 540

Ser Pro Tyr Trp Val Thr Ile Gly Arg Gly Asn Val Val Thr Gly Gln
545                 550                 555                 560

Ile Cys Arg Leu Gly Asn Asn Thr Tyr Thr Asp Cys Thr Pro Arg Ser
                565                 570                 575

Ile Asn Gly Lys Ser Tyr Tyr Ala Ala Val Arg Asp Asn Val Arg Leu
            580                 585                 590

Gly Arg Trp Ala Asp Val Gly Ala Gly Leu Arg Tyr Asp Tyr Arg Ser
        595                 600                 605

Thr His Ser Asp Asp Gly Ser Val Ser Thr Gly Thr His Arg Thr Leu
    610                 615                 620

Ser Trp Asn Ala Gly Ile Val Leu Lys Pro Thr Asp Trp Leu Asp Leu
625                 630                 635                 640

Thr Tyr Arg Thr Ser Thr Gly Phe Arg Leu Pro Ser Phe Ala Glu Met
                645                 650                 655

Tyr Gly Trp Arg Ala Gly Val Gln Ser Lys Ala Val Lys Ile Asp Pro
            660                 665                 670

Glu Lys Ser Phe Asn Lys Glu Ala Gly Ile Val Phe Lys Gly Asp Phe
        675                 680                 685

Gly Asn Leu Glu Ala Ser Trp Phe Asn Asn Ala Tyr Arg Asp Leu Ile
    690                 695                 700

Val Arg Gly Tyr Glu Ala Gln Ile Lys Asp Gly Lys Glu Glu Ala Lys
705                 710                 715                 720

Gly Asp Pro Ala Tyr Leu Asn Ala Gln Ser Ala Arg Ile Thr Gly Ile
                725                 730                 735

Asn Ile Leu Gly Lys Ile Asp Trp Asn Gly Val Trp Asp Lys Leu Pro
            740                 745                 750

Glu Gly Trp Tyr Ser Thr Phe Ala Tyr Asn Arg Val Arg Val Arg Asp
        755                 760                 765

Ile Lys Lys Arg Ala Asp Arg Thr Asp Ile Gln Ser His Leu Phe Asp
```

```
                770                 775                 780
Ala Ile Gln Pro Ser Arg Tyr Val Val Gly Leu Gly Tyr Asp Gln Pro
785                 790                 795                 800

Glu Gly Lys Trp Gly Val Asn Gly Met Leu Thr Tyr Ser Lys Ala Lys
                805                 810                 815

Glu Ile Thr Glu Leu Leu Gly Ser Arg Ala Leu Leu Asn Gly Asn Ser
                820                 825                 830

Arg Asn Thr Lys Ala Thr Ala Arg Arg Thr Arg Pro Trp Tyr Ile Val
                835                 840                 845

Asp Val Ser Gly Tyr Tyr Thr Val Lys Lys His Phe Thr Leu Arg Ala
                850                 855                 860

Gly Val Tyr Asn Leu Leu Asn Tyr Arg Tyr Val Thr Trp Glu Asn Val
865                 870                 875                 880

Arg Gln Thr Ala Gly Gly Ala Val Asn Gln His Lys Asn Val Gly Val
                885                 890                 895

Tyr Asn Arg Tyr Ala Ala Pro Gly Arg Asn Tyr Thr Phe Ser Leu Glu
                900                 905                 910

Met Lys Phe
        915

<210> SEQ ID NO 24
<211> LENGTH: 712
<212> TYPE: PRT
<213> ORGANISM: Neisseria meningitidis

<400> SEQUENCE: 24

Met Asn Asn Pro Leu Val Asn Gln Ala Ala Met Val Leu Pro Val Phe
1               5                   10                  15

Leu Leu Ser Ala Cys Leu Gly Gly Gly Ser Phe Asp Leu Asp Ser
                20                  25                  30

Val Asp Thr Glu Ala Pro Arg Pro Ala Pro Lys Tyr Gln Asp Val Phe
            35                  40                  45

Ser Glu Lys Pro Gln Ala Gln Lys Asp Gln Gly Gly Tyr Gly Phe Ala
    50                  55                  60

Met Arg Leu Lys Arg Arg Asn Trp Tyr Pro Gln Ala Lys Glu Asp Glu
65                  70                  75                  80

Val Lys Leu Asp Glu Ser Asp Trp Glu Ala Thr Gly Leu Pro Asp Glu
                85                  90                  95

Pro Lys Glu Leu Pro Lys Arg Gln Lys Ser Val Ile Glu Lys Val Glu
                100                 105                 110

Thr Asp Ser Asp Asn Asn Ile Tyr Ser Ser Pro Tyr Leu Lys Pro Ser
            115                 120                 125

Asn His Gln Asn Gly Asn Thr Gly Asn Gly Ile Asn Gln Pro Lys Asn
    130                 135                 140

Gln Ala Lys Asp Tyr Glu Asn Phe Lys Tyr Val Tyr Ser Gly Trp Phe
145                 150                 155                 160

Tyr Lys His Ala Lys Arg Glu Phe Asn Leu Lys Val Glu Pro Lys Ser
                165                 170                 175

Ala Lys Asn Gly Asp Asp Gly Tyr Ile Phe Tyr His Gly Lys Glu Pro
                180                 185                 190

Ser Arg Gln Leu Pro Ala Ser Gly Lys Ile Thr Tyr Lys Gly Val Trp
            195                 200                 205

His Phe Ala Thr Asp Thr Lys Lys Gly Gln Lys Phe Arg Glu Ile Ile
    210                 215                 220
```

-continued

```
Gln Pro Ser Lys Ser Gln Gly Asp Arg Tyr Ser Gly Phe Ser Gly Asp
225                 230                 235                 240

Asp Gly Glu Glu Tyr Ser Asn Lys Asn Lys Ser Thr Leu Thr Asp Gly
            245                 250                 255

Gln Glu Gly Tyr Gly Phe Thr Ser Asn Leu Glu Val Asp Phe His Asn
        260                 265                 270

Lys Lys Leu Thr Gly Lys Leu Ile Arg Asn Asn Ala Asn Thr Asp Asn
    275                 280                 285

Asn Gln Ala Thr Thr Gln Tyr Tyr Ser Leu Glu Ala Gln Val Thr
290                 295                 300

Gly Asn Arg Phe Asn Gly Lys Ala Thr Ala Thr Asp Lys Pro Gln Gln
305                 310                 315                 320

Asn Ser Glu Thr Lys Glu His Pro Phe Val Ser Asp Ser Ser Leu
                325                 330                 335

Ser Gly Gly Phe Phe Gly Pro Gln Gly Glu Leu Gly Phe Arg Phe
                340                 345                 350

Leu Ser Asp Asp Gln Lys Val Ala Val Val Gly Ser Ala Lys Thr Lys
    355                 360                 365

Asp Lys Pro Ala Asn Gly Asn Thr Ala Ala Ser Gly Gly Thr Asp
370                 375                 380

Ala Ala Ala Ser Asn Gly Ala Ala Gly Thr Ser Ser Glu Asn Gly Lys
385                 390                 395                 400

Leu Thr Thr Val Leu Asp Ala Val Glu Leu Lys Leu Gly Asp Lys Glu
                405                 410                 415

Val Gln Lys Leu Asp Asn Phe Ser Asn Ala Ala Gln Leu Val Val Asp
        420                 425                 430

Gly Ile Met Ile Pro Leu Leu Pro Glu Ala Ser Glu Ser Gly Asn Asn
        435                 440                 445

Gln Ala Asn Gln Gly Thr Asn Gly Gly Thr Ala Phe Thr Arg Lys Phe
    450                 455                 460

Asp His Thr Pro Glu Ser Asp Lys Lys Asp Ala Gln Ala Gly Thr Gln
465                 470                 475                 480

Thr Asn Gly Ala Gln Thr Ala Ser Asn Thr Ala Gly Asp Thr Asn Gly
                485                 490                 495

Lys Thr Lys Thr Tyr Glu Val Glu Val Cys Cys Ser Asn Leu Asn Tyr
                500                 505                 510

Leu Lys Tyr Gly Met Leu Thr Arg Lys Asn Ser Lys Ser Ala Met Gln
        515                 520                 525

Ala Gly Glu Ser Ser Gln Ala Asp Ala Lys Thr Glu Gln Val Glu
    530                 535                 540

Gln Ser Met Phe Leu Gln Gly Glu Arg Thr Asp Glu Lys Glu Ile Pro
545                 550                 555                 560

Ser Glu Gln Asn Ile Val Tyr Arg Gly Ser Trp Tyr Gly Tyr Ile Ala
                565                 570                 575

Asn Asp Lys Ser Thr Ser Trp Ser Gly Asn Ala Ser Asn Ala Thr Ser
            580                 585                 590

Gly Asn Arg Ala Glu Phe Thr Val Asn Phe Ala Asp Lys Lys Ile Thr
        595                 600                 605

Gly Thr Leu Thr Ala Asp Asn Arg Gln Glu Ala Thr Phe Thr Ile Asp
    610                 615                 620

Gly Asn Ile Lys Asp Asn Gly Phe Glu Gly Thr Ala Lys Thr Ala Glu
625                 630                 635                 640

Ser Gly Phe Asp Leu Asp Gln Ser Asn Thr Thr Arg Thr Pro Lys Ala
```

```
            645                 650                 655
Tyr Ile Thr Asp Ala Lys Val Gln Gly Gly Phe Tyr Gly Pro Lys Ala
            660                 665                 670
Glu Glu Leu Gly Gly Trp Phe Ala Tyr Pro Gly Asp Lys Gln Thr Lys
            675                 680                 685
Asn Ala Thr Asn Ala Ser Gly Asn Ser Ser Ala Thr Val Val Phe Gly
            690                 695                 700
Ala Lys Arg Gln Gln Pro Val Arg
705                 710

<210> SEQ ID NO 25
<211> LENGTH: 186
<212> TYPE: PRT
<213> ORGANISM: Neisseria meningitidis

<400> SEQUENCE: 25

Met Asn Met Lys Thr Leu Leu Ala Leu Ala Val Ser Ala Val Cys Ser
1               5                   10                  15
Val Gly Val Ala Gln Ala His Glu His Asn Thr Ile Pro Lys Gly Ala
                20                  25                  30
Ser Ile Glu Val Lys Val Gln Gln Leu Asp Pro Val Asn Gly Asn Lys
            35                  40                  45
Asp Val Gly Thr Val Thr Ile Thr Glu Ser Asn Tyr Gly Leu Val Phe
        50                  55                  60
Thr Pro Asp Leu Gln Gly Leu Ser Glu Gly Leu His Gly Phe His Ile
65                  70                  75                  80
His Glu Asn Pro Ser Cys Glu Pro Lys Glu Lys Glu Gly Lys Leu Thr
                85                  90                  95
Ala Gly Leu Gly Ala Gly Gly His Trp Asp Pro Lys Gly Ala Lys Gln
                100                 105                 110
His Gly Tyr Pro Trp Gln Asp Asp Ala His Leu Gly Asp Leu Pro Ala
            115                 120                 125
Leu Thr Val Leu His Asp Gly Thr Ala Thr Asn Pro Val Leu Ala Pro
        130                 135                 140
Arg Leu Lys His Leu Asp Asp Val Arg Gly His Ser Ile Met Ile His
145                 150                 155                 160
Thr Gly Gly Asp Asn His Ser Asp His Pro Ala Pro Leu Gly Gly Gly
                165                 170                 175
Gly Pro Arg Met Ala Cys Gly Val Ile Lys
            180                 185

<210> SEQ ID NO 26
<211> LENGTH: 16
<212> TYPE: DNA
<213> ORGANISM: Neisseria meningitidis

<400> SEQUENCE: 26
tttgcggggg gggggg                                                   16

<210> SEQ ID NO 27
<211> LENGTH: 16
<212> TYPE: DNA
<213> ORGANISM: Neisseria meningitidis

<400> SEQUENCE: 27
tttgcgaggg aggtgg                                                   16
```

<210> SEQ ID NO 28
<211> LENGTH: 17
<212> TYPE: DNA
<213> ORGANISM: Neisseria meningitidis

<400> SEQUENCE: 28
ttttgcgagg gaggtgg                                                17

<210> SEQ ID NO 29
<211> LENGTH: 16
<212> TYPE: DNA
<213> ORGANISM: Neisseria meningitidis

<400> SEQUENCE: 29
ggcggaagga atactt                                                 16

<210> SEQ ID NO 30
<211> LENGTH: 35
<212> TYPE: DNA
<213> ORGANISM: Neisseria meningitidis

<400> SEQUENCE: 30
ttgacatttg cgagggaggt ggtataattg aagac                            35

<210> SEQ ID NO 31
<211> LENGTH: 40
<212> TYPE: DNA
<213> ORGANISM: Neisseria meningitidis

<400> SEQUENCE: 31
aaaaatggtt ttttgcgggg ggggggtat aattgaagac                        40

<210> SEQ ID NO 32
<211> LENGTH: 40
<212> TYPE: DNA
<213> ORGANISM: Artificial Sequence
<220> FEATURE:
<223> OTHER INFORMATION: Modified porA promoter

<400> SEQUENCE: 32
aaaaatggtt ttttgcgagg gaggtggtat aattgaagac                       40

<210> SEQ ID NO 33
<211> LENGTH: 40
<212> TYPE: DNA
<213> ORGANISM: Neisseria meningitidis

<400> SEQUENCE: 33
aaaaattgac atttgcgagg gaggtggtat aattgaagac                       40

<210> SEQ ID NO 34
<211> LENGTH: 40
<212> TYPE: DNA
<213> ORGANISM: Neisseria meningitidis

<400> SEQUENCE: 34
aaaattgaca ttttgcgagg gaggtggtat aattgaagac                       40

<210> SEQ ID NO 35
<211> LENGTH: 40
<212> TYPE: DNA
<213> ORGANISM: Artificial Sequence
<220> FEATURE:
<223> OTHER INFORMATION: Hybrid rRNA promoter

```
<400> SEQUENCE: 35
atatcttgac aggcggaagg aatactttat aattcgcaac                    40

<210> SEQ ID NO 36
<211> LENGTH: 39
<212> TYPE: DNA
<213> ORGANISM: Artificial Sequence
<220> FEATURE:
<223> OTHER INFORMATION: Hybrid rRNA promoter

<400> SEQUENCE: 36
atatcttgac aggcggaagg aatactttat attcgcaac                     39

<210> SEQ ID NO 37
<211> LENGTH: 38
<212> TYPE: DNA
<213> ORGANISM: Artificial Sequence
<220> FEATURE:
<223> OTHER INFORMATION: Hybrid rRNA promoter

<400> SEQUENCE: 37
atatcttgac aggcggaagg aatactttta attcgcac                      38

<210> SEQ ID NO 38
<211> LENGTH: 39
<212> TYPE: DNA
<213> ORGANISM: Artificial Sequence
<220> FEATURE:
<223> OTHER INFORMATION: Hybrid rRNA promoter

<400> SEQUENCE: 38
atatcttgac aggcggaagg aaactttata attcgcaac                     39

<210> SEQ ID NO 39
<211> LENGTH: 56
<212> TYPE: DNA
<213> ORGANISM: Artificial Sequence
<220> FEATURE:
<223> OTHER INFORMATION: Hybrid rRNA promoter

<400> SEQUENCE: 39
gtatcgggtg tttgcccgat gtttttaggt ttttatcaaa tttacaaaag gaagcc  56

<210> SEQ ID NO 40
<211> LENGTH: 42
<212> TYPE: DNA
<213> ORGANISM: Artificial Sequence
<220> FEATURE:
<223> OTHER INFORMATION: Hybrid rRNA promoter

<400> SEQUENCE: 40
aaaaatggtt ttttgcgggg ggggggggt ataattgaag ac                  42

<210> SEQ ID NO 41
<211> LENGTH: 358
<212> TYPE: DNA
<213> ORGANISM: Artificial Sequence
<220> FEATURE:
<223> OTHER INFORMATION: Promoter region

<400> SEQUENCE: 41
cgtctgagtc cccgagtttc agacagcata ttcacaaagg cgcaccagcc ggaggaggga  60
gaggaaagga ttgttggagg cggcgcagta tttagcagaa ataaaaaacc ttatccgaca  120
gcgacatgac gaatttcccc aaaaaaatcc cgctgaaagc attgaccgtt tttccctgtg  180
```

```
ggcgtatagt tcggttcttc gctgctgcag aagtggcgga cgaactgaaa agtatagcac    240
agaatgttgg ggatatcgag agatatcttg acaggcggaa ggaatacttt ataattcgca    300
acgtatcggg tgtttgcccg atgtttttag gtttttatca aatttacaaa aggaagcc     358
```

<210> SEQ ID NO 42
<211> LENGTH: 356
<212> TYPE: DNA
<213> ORGANISM: Artificial Sequence
<220> FEATURE:
<223> OTHER INFORMATION: Promoter region
<220> FEATURE:
<221> NAME/KEY: misc_feature
<222> LOCATION: 318, 319, 321
<223> OTHER INFORMATION: 'n' is a, c, g or t

<400> SEQUENCE: 42

```
cgtctgagtc cccgagtttc agacagcata ttcacaaagg cgcaccagcc ggaggaggga     60
gaggaaagga ttgttggagg cggcgcagta tttagcagaa ataaaaaacc ttatccgaca    120
gcgacatgac gaatttcccc aaaaaaatcc cgctgaaagc attgaccgtt tttccctgtg    180
ggcgtatagt tcggttcttc gctgctgcag aagtggcgga cgaactgaaa agtatagcac    240
agaatgttgg ggatatcgag agatatcttg acaggcggaa ggaatacttt atattcgcaa    300
cgtatcgggt gtttgccnna ngttttagg tttttatcaa atttcaaaag gaagcc         356
```

<210> SEQ ID NO 43
<211> LENGTH: 373
<212> TYPE: DNA
<213> ORGANISM: Artificial Sequence
<220> FEATURE:
<223> OTHER INFORMATION: Promoter region
<220> FEATURE:
<221> NAME/KEY: misc_feature
<222> LOCATION: 361
<223> OTHER INFORMATION: 'n' is a, c, g or t

<400> SEQUENCE: 43

```
cgtctgagtc cccgagtttc agacagcata ttcacaaagg cgcaccagcc ggaggaggga     60
gaggaaagga ttgttggagg cggcgcagta tttagcagaa ataaaaaacc ttatccgaca    120
gcgacatgac gaatttcccc aaaaaaatcc cgctgaaagc attgaccgtt tttccctgtg    180
ggcgtatagt tcggttcttc gctgctgcag aagtggcgga cgaactgaaa agtatagcac    240
agaatgttgg ggatatcgag agatatcttg acaggcggaa ggaatacttt taattcgcac    300
gtatcgggtg tttgcccgat gtttttaggt ttttattaaa tttacaaaag gaagcccata    360
ngaatcgaac tgc                                                       373
```